(12) United States Patent
Shah et al.

(10) Patent No.: US 11,571,390 B2
(45) Date of Patent: *Feb. 7, 2023

(54) ABUSE DETERRENT COMPOSITIONS AND METHODS OF USE

(71) Applicant: OHEMO LIFE SCIENCES INC., Juncos, PR (US)

(72) Inventors: Manish S. Shah, West Caldwell, NJ (US); Ray J. DiFalco, Ridgewood, NJ (US); Stefan Aigner, Valley Cottage, NY (US)

(73) Assignee: Othemo Life Sciences, Inc., Juncos, PR (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/218,792

(22) Filed: Mar. 18, 2014

(65) Prior Publication Data

US 2014/0275039 A1  Sep. 18, 2014

Related U.S. Application Data

(60) Provisional application No. 61/799,096, filed on Mar. 15, 2013.

(51) Int. Cl.
| | |
|---|---|
| *A61K 9/20* | (2006.01) |
| *A61K 31/485* | (2006.01) |
| *A61K 9/28* | (2006.01) |
| *A61K 9/50* | (2006.01) |
| *A61K 45/06* | (2006.01) |

(52) U.S. Cl.
CPC .......... *A61K 9/2086* (2013.01); *A61K 9/2846* (2013.01); *A61K 9/5073* (2013.01); *A61K 31/485* (2013.01); *A61K 45/06* (2013.01)

(58) Field of Classification Search
CPC .. A61K 9/2086; A61K 9/2846; A61K 9/5073; A61K 31/485
See application file for complete search history.

(56) References Cited

U.S. PATENT DOCUMENTS

| | | |
|---|---|---|
| 3,980,766 A | 9/1976 | Shaw et al. |
| 4,070,494 A | 1/1978 | Hoffmeister et al. |
| 4,361,546 A | 11/1982 | Stricker et al. |
| 4,423,099 A | 12/1983 | Mueller et al. |
| 4,459,279 A | 7/1984 | Stricker et al. |
| 4,784,858 A | 11/1988 | Ventouras |
| 4,865,849 A | 9/1989 | Conte et al. |
| 4,996,047 A | 2/1991 | Kelleher et al. |
| 5,068,112 A | 11/1991 | Samejima et al. |
| 5,206,030 A | 4/1993 | Wheatley |
| 5,395,626 A | 3/1995 | Kotwal |
| 5,474,786 A | 12/1995 | Kotwal |
| 5,484,608 A | 1/1996 | Rudnic et al. |
| 5,614,218 A | 3/1997 | Olsson et al. |
| 5,639,476 A | 6/1997 | Oshlack et al. |
| 5,645,858 A | 7/1997 | Kotwal et al. |
| 5,866,161 A | 2/1999 | Childers et al. |
| 5,955,104 A | 9/1999 | Momberger |
| 5,958,459 A | 9/1999 | Chasin et al. |
| 6,066,339 A | 5/2000 | Stark et al. |
| 6,277,384 B1 | 8/2001 | Kaiko et al. |
| 6,309,668 B1 | 10/2001 | Bastin et al. |
| 6,310,072 B1 | 10/2001 | Smith |
| 6,375,957 B1 | 4/2002 | Kaiko et al. |
| 6,419,954 B1 | 7/2002 | Chu et al. |
| 6,475,494 B2 | 11/2002 | Kaiko et al. |
| 6,531,152 B1 | 3/2003 | Lerner et al. |
| 6,720,005 B1 | 4/2004 | Ayres |
| 6,753,011 B2 | 6/2004 | Faour |
| 6,911,217 B1 | 6/2005 | Gren |
| 6,929,803 B2 | 8/2005 | Wong et al. |
| 7,316,821 B2 | 1/2008 | Oshlack et al. |
| 7,955,619 B2 * | 6/2011 | Shah et al. ............... 424/463 |
| 2003/0068371 A1 | 4/2003 | Oshlack |
| 2003/0068375 A1 | 4/2003 | Wright et al. |
| 2003/0092724 A1 | 5/2003 | Kao |
| 2003/0099711 A1 | 5/2003 | Meadows et al. |
| 2003/0118641 A1 | 6/2003 | Maloney |
| 2003/0157167 A1 | 8/2003 | Kao et al. |
| 2003/0180359 A1 | 9/2003 | Vergnault |
| 2003/0180362 A1 | 9/2003 | Park et al. |
| 2003/0198674 A1 | 10/2003 | Curatolo et al. |
| 2004/0052731 A1 | 3/2004 | Hirsch |
| 2004/0092542 A1 | 5/2004 | Oshlack et al. |
| 2004/0131552 A1 | 7/2004 | Boehm |
| 2004/0161382 A1 | 8/2004 | Yum et al. |
| 2004/0213849 A1 | 10/2004 | Sowden et al. |
| 2004/0228802 A1 | 11/2004 | Chang et al. |
| 2005/0020613 A1 | 1/2005 | Boehm et al. |
| 2005/0038121 A1 | 2/2005 | Mickle et al. |
| 2005/0074493 A1 | 4/2005 | Mehta |
| 2005/0080012 A1 | 4/2005 | Mickle |
| 2005/0112067 A1 | 5/2005 | Kumar et al. |
| 2005/0163843 A1 | 7/2005 | Boehm et al. |
| 2005/0176646 A1 | 8/2005 | Mickle et al. |

(Continued)

FOREIGN PATENT DOCUMENTS

| | | |
|---|---|---|
| CA | 2 554 697 A1 | 4/2007 |
| DE | 102006051020 A1 | 4/2008 |

(Continued)

OTHER PUBLICATIONS

Fujita T, Pubmed abstract (Nippon Rinsho) Mar. 1998; 56(3).*

(Continued)

*Primary Examiner* — Shobha Kantamneni

(74) *Attorney, Agent, or Firm* — William Beaumont; Juneau & Mitchell

(57) ABSTRACT

Orally administrable pharmaceutical compositions, methods of administration, and methods of making the same are provided. The pharmaceutical compositions provide abuse deterrent properties.

20 Claims, 1 Drawing Sheet

(56) References Cited

U.S. PATENT DOCUMENTS

| | | |
|---|---|---|
| 2005/0191349 A1 | 9/2005 | Boehm et al. |
| 2005/0214223 A1 | 9/2005 | Bartholomaus |
| 2005/0220715 A1 | 10/2005 | Lin |
| 2005/0245483 A1 | 11/2005 | Brogmann et al. |
| 2005/0266072 A1 | 12/2005 | Oshlack et al. |
| 2005/0266080 A1 | 12/2005 | Desai et al. |
| 2005/0281748 A1 | 12/2005 | Hirsh |
| 2006/0014697 A1 | 1/2006 | Mickle |
| 2006/0104909 A1 | 5/2006 | Vaghefi et al. |
| 2006/0110327 A1 | 5/2006 | Emigh |
| 2006/0165602 A1 | 7/2006 | Galer |
| 2006/0189635 A1 | 8/2006 | Kramer et al. |
| 2006/0251721 A1 | 11/2006 | Cruz et al. |
| 2007/0004797 A1 | 1/2007 | Weyers et al. |
| 2007/0020339 A1 | 1/2007 | Bear |
| 2007/0066537 A1 | 3/2007 | Mickle et al. |
| 2007/0128269 A1 | 6/2007 | Gervais et al. |
| 2007/0148097 A1 | 6/2007 | Finn et al. |
| 2007/0212414 A1 | 9/2007 | Baichwal et al. |
| 2007/0215511 A1 | 9/2007 | Mehta et al. |
| 2007/0259045 A1 | 11/2007 | Mannion |
| 2007/0269505 A1 | 11/2007 | Flath et al. |
| 2008/0057123 A1 | 3/2008 | Grenier et al. |
| 2008/0069871 A1 | 3/2008 | Vaughn et al. |
| 2008/0069891 A1 | 3/2008 | Habib et al. |
| 2008/0085305 A1 | 4/2008 | Baichwal |
| 2008/0233197 A1* | 9/2008 | Matthews ............ A61K 9/4808 424/490 |
| 2008/0260819 A1 | 10/2008 | Fleming et al. |
| 2008/0311205 A1 | 12/2008 | Habib et al. |
| 2009/0022798 A1 | 1/2009 | Rosenberg et al. |
| 2009/0081290 A1 | 3/2009 | McKenna et al. |
| 2009/0082466 A1 | 3/2009 | Babul |
| 2009/0232887 A1 | 9/2009 | Odidi et al. |
| 2009/0297617 A1 | 12/2009 | Rariy et al. |
| 2010/0015223 A1 | 1/2010 | Cailly-Dufestel et al. |
| 2010/0099696 A1 | 4/2010 | Soscia |
| 2010/0112052 A1 | 5/2010 | Chen et al. |
| 2010/0221324 A1 | 9/2010 | Petereit et al. |
| 2010/0226978 A1 | 9/2010 | Petereit et al. |
| 2011/0184007 A1 | 7/2011 | Shah et al. |
| 2012/0003311 A9 | 1/2012 | Yoshitake et al. |
| 2012/0202839 A1 | 8/2012 | Emigh et al. |

FOREIGN PATENT DOCUMENTS

| | | |
|---|---|---|
| EP | 0092060 | 10/1983 |
| EP | 682945 A2 | 11/1995 |
| FR | 2787715 | 6/2000 |
| WO | WO 95/20947 | 8/1995 |
| WO | WO 95/25506 | 9/1995 |
| WO | WO 00/027364 | 5/2000 |
| WO | WO 03/13479 | 2/2003 |
| WO | WO 2004/037259 A1 | 5/2004 |
| WO | WO 05/055981 | 6/2005 |
| WO | WO 2005/117841 A | 12/2005 |
| WO | WO 06/089493 | 8/2006 |
| WO | WO 2006/079550 A2 | 8/2006 |
| WO | WO 2008/049657 A2 | 5/2008 |
| WO | WO 09/092818 | 7/2009 |

OTHER PUBLICATIONS

Page et.al. Reviews, DDT vol. 6, No. Jan. 2, 2001, p. 92.*
"Guidance for Industry Dissolution Testing of Immediate Release Solid Oral Dosage Forms," (hereinafter "FDA Guidance"), cited in 2012.
Abbaspour et al., "Preparation and characterization of ibuprofen pellets based on Eudragit RS PO and RL PO or their combination," International Journal of Pharmaceutics, 2005, 303:88-94.
Avinza ("extended release morphine sulfate" marketed by Ligand Pharmaceuticals Inc., hereinafter "Avinza"), cited in 2013.
Babak et al., "Impact of bulk and surface properties of some biocompatible hydrophobic polymers on the stability of methylene chloride-in-water mini-emulsions used to prepare nanoparticles by emulsification-solvent evaporation," Colloids and Surfaces B: Biointerfaces, 2007, 59:194-207.
Chithaluru et al., "Formulation and Invitro Evaluation of Sustained Release Matrix Tablets of Losartan Potassium," Asian Journal of Pharmaceutical and Clinical Research, 2011, 4:18-22.
Conte et al., "Multi-layered hydrophilic matrices as constant release devices (Geomatric™ Systems)," Journal of Controlled Release, 26 (1993), pp. 39-47.
Conte et al., "Modulation of the dissolution profiles from Geomatrix® multi-layer matrix tablets containing drugs of different solubility," Biomaterials, 17(9) (1996), pp. 889-896.
Conte et al., "Press-coated tablets for time-programmed release of drugs," Biomaterials, 14(13) (1993), pp. 1017-1023.
Cozzolino et al., "Dye release behavior from polyvinyl alcohol films in a hydro-alcoholic medium: Influence of physicochemical heterogeneity," Colloids and Surfaces A: Physicochemical and Engineering Aspects, 2012, 403:45-53.
Cremer, "Pharmaceutical Applications of Layer Tablets," www.pharma-meggie.com, 249 (May 2001), pp. 1-4.
Efentakis et al., "Formulation study and evaluation of matrix and three-layer tablet sustained drug delivery systems based on Carbopols and isosorbide mononitrate," AAPS PharmSciTech, 9(3) (2008), pp. 917-923.
Evonik et al., "Eudragit RS PO" accessed at http://eudragit.evonik.com/product/eudragit/en/products-services/eudragit-products/sustained-release-formulations/rs-po/pages/default.aspx 2013.
Fisher et al., Roxicodone. "A Chronic Pain Management Manual," Writers Club Press, iUniverse, Lincoln, NE (2002) Appx. E.
Heng et al., "Mechanism of pellet coat rupture and its effect on drug release," Chem Pharm Bull, 47(7) (1999), pp. 939-943.
Kalantzi et al., "Recent advances in oral pulsatile drug delivery," Recent Patents on Drug Delivery and Formulation, 3 (2009), pp. 49-63.
Kral et al., "Oxycodone Safety Handout for Patients," (2007) accessed at www.Pain-Topics.org on May 7, 2013.
Murtaza, "Ethylcellulose Microparticles: A Review," Acta Poloniae Pharmaceutica—Drug Research, 2012, 69:11-22.
Opadry (Colorcon, accessed at http://www.colorcom.com/products/coatings/immediate-release/Opadry, accessed in 2013.
Opana ER ("Oxymorphone Hydrochloride) Extended-Release" Tablets marketed by Endo Pharmaceuticals, Inc., accessed at http://dailymed.nlm.nih.gov/dailymed/lookup.cfm?setid=545cea18-11ad-4881-b184-6f8bcc7908e4 accessed on Feb. 22, 2013.
Roxicodone Package Insert (Xanodyne (2009) accessed at http://dailymed.nlm.nih.gov/dailymed/archives/fdaDrugInfo.cfm?archiveid=12847 on May 7, 2013.
Singh et al., "A diffusion controlled drug delivery system for theophylline," Drug Development and Industrial Pharmacy, 20(7) (1994), pp. 1225-1238.
Substrate—Chambers 21st Century Dictionary, London: Chambers Harrap, 2001, Credo Reference. Jan. 1, 2002, Web. Jul. 30, 2013 (www.credoreference.com/entry/chambdict/substrate).
Sutter et al., "Polymer films as diffusion barriers for oral controlled release preparations with special reference to aqueous dispersions," Acta Pharmaceutica Technologica, 34(4) (1988), pp. 179-188 (abstract).
Yang et al., "Accessibility of solid core tablet for dissolution in an asymmetric triple-layer matrix system," Journal of Pharmacy and Pharmacology,55(1) (2003), pp. 1331-1337.
"Eudragit® NE 30D: Specification and Test Methods" Evonik Industries AG, Web, May 2014, http://www.eudragit.com. 5 pages.
"Oxycontin® (Oxycodone HCI Controlled-Release Tablets)" Monograph, Purdue Pharma, 2007, accessed at http://accessdata.fda.gov/drugsatfda_docs/label/2009/020553s060lbl.pdf. 32 pages.
Amabile et al. "Overview of Oral Modified-Release Opioid Products for the Management of Chronic Pain," Ann Pharmacother, 2006; 40:1327-1335.
Bajpai et al. "Responsive Polymers in Controlled Drug Delivery," Progress in Polymer Science 2008; 33:1088-1118.
Crowley et al. "Drug-Excipient Interactions," Pharmaceutical Technology, 2001, pp. 1-6.

(56) References Cited

OTHER PUBLICATIONS

Gimbel et al. "The Efficacy and Safety of Oral Immediate-Release Oxymorphone for Postsurgical Pain," AnesthAnalg, 2004; 99: 1472-1477.

Harris et al. "Abuse Potential, Pharmacokinetics, Pharmacodynamics, and Safety of Intranasaliy Administered Crushed Oxycodone HCI Abuse-Deterrent Controlled-Release Tablets in Recreational Opioid Users," The Journal of Clinical Pharmacology, 2013; 54(4):468-477.

Lenaerts et al. "Cross-linked high amylose starch for controlled release of drugs: recent advances," Journal of Controlled Release, 1998; 53: 225-234.

Meijerman et al. "Herb-Drug Interactions in Oncology: Focus on Mechanisms of Induction," The Oncologist, 2006; 11:742-752.

Overgaard et al. "Patient's evaluation of shape, size and colour of solid dosage forms," Pharm World Sci, 2001; 23(5): 185-188. 8 pages.

Savage et al. "Challenges in Using Opioids to Treat Pain in Persons with Substance Use Disorders," Addict. Sci. Clin. Pract., 2008; 4(2): 4-25.

Solinis et al. "Release in ketoprofen enantiomers from HPMC K100M matrices—diffusion studies," International Journal of Pharmaceutics, 2002; 239:61-68.

Van Zee, "The Promotion and Marketing of OxyContin: Commercial Triumph, Public Health Tragedy," American Journal of Public Health, 2009; 99:221-227.

\* cited by examiner

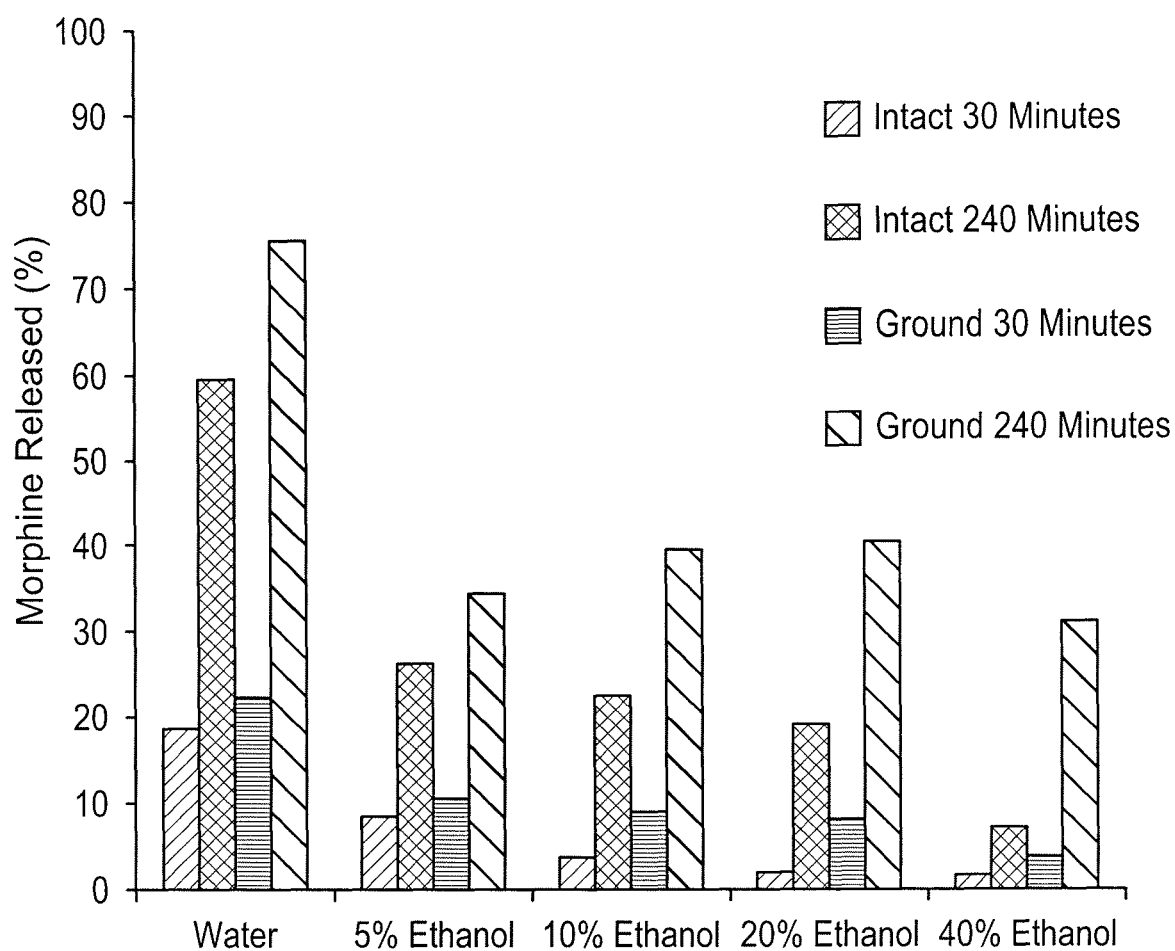

ABUSE DETERRENT COMPOSITIONS AND METHODS OF USE

CROSS REFERENCE TO RELATED APPLICATION

This application claims the benefit of U.S. Patent Provisional Application No. 61/799,096, filed on Mar. 15, 2013, which is incorporated herein by reference.

FIELD OF THE INVENTION

The present invention provides orally administrable pharmaceutical compositions, methods of administration, and methods of making the same.

BACKGROUND OF THE INVENTION

The present invention relates to orally administrable pharmaceutical compositions, and specifically relates to compositions that are designed to reduce the potential for improper administration of medications and their use in a non-indicated or non-prescribed manner. The present invention can comprise any drug, and it is especially useful with medications that are subject to abuse, such as drugs affecting the central nervous system. For example, the present invention is particularly useful for pain medications, medications to reduce or eliminate anxiety attacks, stimulants and sleeping pills. With these general types of drugs, there is the potential of abuse and improper administration that may result in drug overdose, addiction, suboptimal efficacy, and/or death.

Opioid agonists are substances that act by attaching to specific proteins called opioid receptors, which are found in the brain, spinal cord, and gastrointestinal tract. When these drugs attach to certain opioid receptors in the brain and spinal cord, they can effectively block the transmission of pain messages to the brain. Opioid analgesics such as oxycodone, morphine, oxymorphone, hydrocodone and hydromorphone are successful and therapeutically useful pain medications. Opioids undergo phase 1 metabolism by the cytochrome P450 (CYP) pathway, phase 2 metabolism by conjugation, or both, as described in Smith H, "Opioid Metabolism," *Mayo Clin. Proc.,* 2009; 84(7):613-624.

Morphine, also known as (5α,6α)-7,8-didehydro-4,5-epoxy-17-methylmorphinan-3,6-diol, is an example of a potent opioid analgesic used in the treatment of acute, chronic, and severe pain. Major metabolites of morphine include morphine-3-glucuronide (M3G), morphine-6-glucuronide (M6G), hydromorphone, normorphine (NM) and minor metabolites such as morphine-3,6-diglucuronide, morphine-3-ethereal sulfate, normorphine-6-glucuronide, and normorphine-3-glucuronide. Morphine-6-glucuronide (M6G), a major metabolite of morphine, is formed by glucuronidation. M6G and morphine both demonstrate analgesic activity.

Oxycodone, also known as (5R,9R,13S,14S)-4,5α-epoxy-14-hydroxy-3-methoxy-17-methylmorphinan-6-one, is an opioid analgesic used for the treatment of pain. Major metabolites of oxycodone include noroxycodone, a oxycodol, β oxycodol, oxymorphone, α oxymorphol, β oxymorphol, noroxymorphone, α noroxycodol, β noroxycodol, noroxymorphone, 14-hydroxydihydrocodeine, and 14-hydroxydihydromorphine. Oxymorphone and noroxycodone are the most commonly known major metabolites of oxycodone.

Oxymorphone, also known as 14-hydroxydihydromorphinone and 4,5α-epoxy-3,14-dihydroxy-17-methylmorphinan-6-one, is an opioid analgesic used for the treatment of pain. Major metabolites of oxymorphone include oxymorphone-3-glucuronide and 6-hydroxy-oxymorphone.

Hydrocodone, which is also known as 4,5α-epoxy-3-methoxy-17-methylmorphinan-6-one, is an opioid analgesic used for the treatment of pain. Major metabolites of hydrocodone include norhydrocodone and hydromorphone.

Hydromorphone, which is also known as 4,5-α-epoxy-3-hydroxy-17-methyl morphinan-6-one, is an opioid analgesic. Major metabolites of hydromorphone include hydromorphone-3-glucuronide, hydromorphone-3-glucoside and dihydroisomorphine-6-glucuronide.

Codeine, which is also known as a (5α,6α)-7,8-didehydro-4,5-epoxy-3-methoxy-17-methylmorphinan-6-ol, is an opioid used for its its analgesic, antitussive, antidiarrheal, antihypertensive, anxiolytic, antidepressant, sedative and hypnotic properties. Major metabolites of codeine include codeine-6-glucuronide (C6G), norcodeine, hydrocodone, morphine, morphine-3-glucuronide, morphine-6-glucuronide, and normorphine.

Central nervous stimulants are often used to increase mental alertness, and they can results in feelings of exhilaration and energy. Examples of such drugs include amphetamines such as methylphenidate, dextroamphetamine, and lisdexamfetamine.

Methylphenidate, which is also known as methyl phenyl (piperidin-2-yl)acetate, is a drug often used for treatment of narcolepsy, attention-deficit/hyperactivity disorder, and depression. Major metabolites of methylphenidate include but are not limited to ethylphenidate, ritalinic acid (α-phenyl-2-piperidine acetic acid), hydroxymethylphenidate, and hydroxyritalinic acid.

Dextroamphetamine, which is also known as (2S)-1-phenylpropan-2-amine, is a drug used for treatment of narcolepsy, attention-deficit/hyperactivity disorder, and depression. Major metabolites of dextroamphetamine include but are not limited to 4-hydroxyamphetamine, benzoic acid, phenylacetone, hippuric acid, 4-hydroxynorephedrine, and norephedrine.

Lisdexamfetamine, also known as lisdexamfetamine, is another stimulant. It is a prodrug of phenethylamine and amphetamines such as dextroamphetamine.

Benzodiazepines are commonly used to treat anxiety. Examples of benzodiazepines include, but are not limited to alprazolam, lorazepam, and diazepam.

Alprazolam, which is also known as 8-chloro-1-methyl-6-phenyl-4H-[1,2,4]triazolo[4,3-a][1,4]benzodiazepine, is a short acting anxiolytic. Major metabolites of alprazolam include, but are not limited to 4-hydroxyalprazolam and α-hydroxyalprazolam.

Lorazepam, which is also known as (RS)-7-Chloro-5-(2-chlorophenyl)-3-hydroxy-1,3-dihydro-2H-1,4-benzodiazepin-2-one, is an anxiolytic agent having intermediate duration of action. Major metabolites of lorazepam include, but are not limited to, 3-O-phenolic glucuronide and lorazepam glucuronide.

Diazepam, which is also known as 7-chloro-1,3-dihydro-1-methyl-5-phenyl-1,4-benzodiazepin-2(3H)-one, is a commonly used anxiolytic. Major metabolites of diazepam include, but are not limited to desmethyldiazepam, esmethyldiazepam, oxazepam, and temazepam.

While pain medications, medications to reduce or eliminate anxiety attacks (psychotherapeutic drugs), stimulants and sleeping pills can be safe, effective, and therapeutically useful when administered properly, such drugs are susceptible to abuse. Examples of such compositions include but are not limited to ROXICODONE® (oxycodone tablets), OXYCONTIN® (oxycodone tablets), DILAUDID® (hydromorphone tablets), OPANA® and OPANA ER® (oxymorphone tablets), MS CONTIN® (morphine tablets), CONCERTAO, METHYLIN®, RITALIN®, RITALIN LA®, and EQUASYM KL® (methylphenidate tablets and capsules), FOCALIN® (dexmethylphenidate capsules), ADDERALL®, DEXEDRINE®, and DEXTROSTAT® (dextroamphetamine tablets and capsules), VYVANSE® (lisdexamfetamine capsules), ATIVAN® (lorazepam), XANAX® (alprazolam), and VALIUM® (diazepam).

A sense of euphoria or "high" can be experienced with high serum concentrations of these drugs. Individuals seeking to abuse these drugs will often tamper with oral dosage forms containing the drugs to achieve this "high." For example, a large amount of tablets can be placed in a liquid to form a solution, and abusers either consume the liquid or more often filter and inject the solution. These tablets can also be crushed into a powder or small particle sizes and snorted intranasally. Nasal insufflation, which is another term for the inhalation of substances through the nose, is a common and harmful practice among abusers. Long-term practice of nasal insufflation can result in permanent damage to nasal tissue and increased incidence of toxicity and overdose. There is a need in the art for pharmaceutical compositions which minimize the ability for abuse, and when administered properly, provide an adequate and effective amount of drug.

It is an object of the present invention to provide a pharmaceutical composition that reduces the potential for improper administration drugs but which, when administered as directed through oral administration, is capable of delivering a therapeutically effective dose to a subject. In particular, the present invention addresses the need for an orally administrable drug product which, compared to conventional formulations, decreases the ability of an individual to achieve a "high" or euphoria effect through injection or insufflation.

SUMMARY OF THE INVENTION

The present invention provides an oral pharmaceutical composition in unit dosage form comprising a drug, a pH-dependent agent, and a pH-independent agent, wherein about 60% or more of the total amount of drug in the pharmaceutical composition is released after 60 minutes under the following dissolution conditions: 0.1N HCl, 500 mL, USP Apparatus 2 (paddle), 50 rpm, 37° C.; and wherein about 25% or less of the total amount of drug in the pharmaceutical composition is released after 60 minutes under the following dissolution conditions: DI water, 500 mL, USP Apparatus 2 (Paddle), 50 rpm, 37° C.

The present invention also provides an oral pharmaceutical composition in unit dosage form comprising a drug, a pH-dependent agent, and a pH-independent agent, wherein about 50% or more of the total amount of drug in the pharmaceutical composition is released after 8 hours under the following dissolution conditions: 0.1N HCl, 500 mL, USP Apparatus 2 (paddle), 50 rpm, 37° C.; and wherein about 25% or less of the total amount of drug in the pharmaceutical composition is released after 60 minutes under the following dissolution conditions: DI water, 500 mL, USP Apparatus 2 (Paddle), 50 rpm, 37° C.

The present invention also provides an orally administrable pharmaceutical composition comprising a drug, wherein the composition is configured such that when the pharmaceutical composition is administered intranasally in physically compromised form to a subject, the area under the curve (AUC) of drug after a period of time is less than 200% of the AUC of the drug achieved after oral administration of an intact form of the pharmaceutical composition after the same period of time.

The present invention provides an orally administrable pharmaceutical composition comprising a drug, wherein the composition is configured such that when the pharmaceutical composition is administered intranasally in physically compromised form to a subject, the area under the curve (AUC) of a major metabolite of the drug after a period of time is at least 15% of the AUC of the major metabolite achieved after oral administration of an intact form of the pharmaceutical composition after the same period of time.

The present invention also provides an orally administrable pharmaceutical composition comprising a drug, wherein the composition is configured such that when the pharmaceutical composition is administered intranasally in physically compromised form to a subject, the ratio of the area under the curve (AUC) of the drug to the AUC of a major metabolite of the drug (drug:major metabolite) achieved after a period of time is less than 25 times the ratio of the AUC of the drug to the AUC of the major metabolite (drug:major metabolite) achieved after the same period of time after oral administration of the pharmaceutical composition in an intact form.

The present invention also provides an orally administrable pharmaceutical composition comprising a drug, wherein the composition is configured such that when the pharmaceutical composition is administered intranasally in physically compromised form to a subject, the sum of the area under the curve (AUC) of the drug and the AUC of a major metabolite of the drug after a period of time is less than the sum of the AUC of the drug and the AUC of the major metabolite achieved after the same period of time after oral administration of the pharmaceutical composition in an intact form.

The present invention also provides an orally administrable pharmaceutical composition comprising a drug, wherein the composition is configured such that when the pharmaceutical composition is administered intranasally in physically compromised form to a subject, the ratio of the area under the curve (AUC) of the drug to the AUC of a major metabolite of the drug (drug:major metabolite) achieved after a period of time is about 10 or less.

The present invention also provides a plurality of particles having a particle size distribution (D50) of about 100 μm to about 1000 μm, wherein the particles each comprise a drug and one or more pharmaceutically acceptable excipients and wherein the particles are configured such that the amount of drug released from the plurality of particles is no greater than 500% of the amount of drug released from an intact unit dosage form comprising the same amount (w/w) as the plurality of particles, under the following identical conditions: 30 mL of ethanol, 25° C., agitated at 100 rpm for a period of time.

The present invention also provides a plurality of particles having a particle size distribution (D50) of about 100 μm to about 1000 μm, wherein the particles each comprise a drug and one or more pharmaceutically acceptable excipients and wherein the particles are configured such that the rate of drug released from the plurality of particles is no greater than 500% of the rate of drug released from an intact unit dosage form comprising the same amount (w/w) as the plurality of particles, under the following identical conditions: 30 mL of ethanol, 25° C., agitated at 100 rpm for a period of time.

The present invention also provides a plurality of particles comprising: an active layer comprising a drug and a first polymer, and a barrier layer comprising a second polymer, wherein the active layer and barrier layer are bonded, and wherein the particles are configured such that the amount of drug released from the plurality of particles is no greater than 500% of the amount of drug released an intact unit dosage form comprising the same amount (w/w) as the plurality of particles, under the following identical conditions: 30 mL of ethanol, 25° C., agitated at 100 rpm for a period of time.

The present invention also provides a plurality of particles comprising: an active layer comprising a drug and a first polymer, and a barrier layer comprising a second polymer, wherein the active layer and barrier layer are bonded, and wherein the particles are configured such that the rate of drug released from the plurality of particles is no greater than 500% of the rate of drug released from an intact unit dosage form comprising the same amount (w/w) as the plurality of particles, under the following identical conditions: 30 mL of ethanol, 25° C., agitated at 100 rpm for a period of time.

In some embodiments, the orally administrable compositions comprise two or more of the above features.

The present invention also provides a method of treating a condition, comprising administering to a patient in need thereof a pharmaceutical composition of the invention. The present invention also provides a method of reducing the intensity, frequency and/or quality of euphoria, and a method of decreasing the rate at which euphoria occurs associated with administration of the drug, wherein the method comprises administration of a pharmaceutical composition of the present invention. The present invention also provides a method of reducing the potential of abuse in a subject taking an opioid or stimulant-containing composition.

The present invention also provides a method of making such oral pharmaceutical compositions and a method of treating a medical condition comprising administering to a subject in need thereof the oral pharmaceutical composition of the present invention.

BRIEF DESCRIPTION OF THE FIGURE

FIG. 1 describes the results of the experiment described in Example 4.

DETAILED DESCRIPTION OF THE INVENTION

The present invention provides an abuse deterrent oral pharmaceutical composition in unit dosage form which, when administered orally, can provide a therapeutic amount of a drug to a subject to accomplish a pharmaceutical effect, such as pain relief, while minimizing the ability of a potential abuser to experience a "high" through improper administration of the composition, such as injection or insufflation. The present invention provides for pharmaceutical compositions, which when administered orally as directed, will provide a therapeutically effective amount of a drug to a subject within the intended time when the pharmaceutical composition is in an acidic pH. However, when the surrounding environment of the oral pharmaceutical composition is at a neutral or alkaline pH, such as if the composition is placed in a water or basic liquid medium, then the release of the drug from the dosage form may be retarded or reduced.

The present invention provides immediate-release and extended-release formulations. The pharmaceutical composition of the invention can comprise either or both extended release formulations, with a typical in vivo or in vitro slow release of drug over a period of about 6 to about 24 hours, preferably at least 80% of the drug released at about 6 to about 24 hours, as well as conventional immediate release formulations, preferably with a release of at least 80%, more preferably at least 90% and most preferably at least 95%, of the drug in one hour, designed for oral administration.

The present invention provides an oral pharmaceutical composition in unit dosage form comprising a drug, a pH-dependent agent, and a pH-independent agent, wherein about 60% or more of the total amount of drug in the pharmaceutical composition is released after 60 minutes under the following dissolution conditions: 0.1N HCl, 500 mL, USP Apparatus 2 (paddle), 50 rpm, 37° C.; and wherein about 25% or less of the total amount of drug in the pharmaceutical composition is released after 60 minutes under the following dissolution conditions: DI water, 500 mL, USP Apparatus 2 (Paddle), 50 rpm, 37° C. In particular, in some embodiments, when the pharmaceutical composition is placed in the hydrochloric acid medium, about 60% or more, preferably about 70% or more, preferably about 80% or more, more preferably about 90% or more of the total amount of drug in the pharmaceutical composition is released after 60 minutes. In some embodiments, when the pharmaceutical composition is placed in the deionized water medium, about 25% or less, preferably about 15% or less, and more preferably about 10% or less of the total amount of drug in the pharmaceutical composition is released after 60 minutes.

The present invention also provides an oral pharmaceutical composition in unit dosage form comprising a drug, a pH-dependent agent, and a pH-independent agent, wherein no more than 50% of the total amount of drug in the pharmaceutical composition is released within 1 hour and about 50% or more of the total amount of drug in the pharmaceutical composition is released after 8 hours under the following dissolution conditions: 0.1N HCl, 500 mL, USP Apparatus 2 (paddle), 50 rpm, 37° C.; and wherein about 25% or less of the total amount of drug in the pharmaceutical composition is released after 60 minutes under the following dissolution conditions: DI water, 500 mL, USP Apparatus 2 (Paddle), 50 rpm, 37° C. In particular, in some embodiments, when the pharmaceutical composition is placed in the hydrochloric acid medium, about 60% or more, preferably about 70% or more, more preferably about 80% or more of the total amount of drug in the pharmaceutical composition is released after 8 hours. In some embodiments, when the pharmaceutical composition is placed in the deionized water medium, about 25% or less, preferably about 15% or less, and more preferably about 10% or less of the total amount of drug in the pharmaceutical composition is released after 60 minutes.

The combination of the pH-dependent agent and pH-independent agent may contribute to the abuse deterrent aspect of the pharmaceutical composition. When the pharmaceutical composition is in a surrounding environment which is at or exceeds a particular pH, then the pH-dependent agent and pH-independent agent may contribute to inhibiting the release of the drug from the pharmaceutical composition. In some embodiments, when the pharmaceutical composition is placed in an acidic medium in vivo or in vitro, such as below a pH of about 6, more preferably about 5 or below, even more preferably about 4 or below, and most preferably about 3.5 or below, the pharmaceutical composition releases about 60% or more of the total amount of drug in the composition after a time period of about 60 minutes for immediate release formulations and about 8 hours for extended release formulations. In some embodiments, about 75% or more, more preferably about 90% or more of the total amount of drug in the pharmaceutical composition is released from the pharmaceutical composition after a time period of about 60 minutes for immediate release formulations and about 8 hours for extended release formulations. In some embodiments, these amounts are released after 30 minutes for immediate release formulations. However, when the surrounding environment of the pharmaceutical composition is at or above a particular pH, such as for example, at or above about 6.5, the release of the drug from the pharmaceutical composition may be affected. The release of the drug is considered to be affected, for example, if the amount and/or rate of release of drug is reduced. In some embodiments, when the pharmaceutical composition is placed in a medium having a pH of about 6 or higher, more preferably about 6.5 or higher, and most preferably about 7 or higher, the pharmaceutical composition releases about 25% or less, more preferably about 15% or less, and most preferably about 10% or less of the total amount of drug in the composition after 60 minutes of placement in the medium. In some embodiments, the medium is deionized water. In some embodiments, the medium is an alkaline medium.

In some embodiments, when the pharmaceutical composition is placed in a medium having a pH of about 6 or higher, preferably between 6.5 and 7.5, the amount and/or rate of release of the drug from the pharmaceutical composition in 60 minutes may be reduced by about 10% or more, preferably about 25% or more, more preferably about 50% or more, and most preferably about 75% or more, compared to the amount and/or rate of release after placement in a medium having a pH below about 5, preferably below about 4. In some embodiments, placement of the pharmaceutical composition in a medium of pH of about 6 or higher, preferably between 6.5 and 7.5, may result in at least 90% reduction in the amount and/or rate of release of drug from the pharmaceutical composition in 60 minutes, compared to the amount and/or rate of release after placement in a medium having a pH below about 5, preferably below about 4.

The "medium" can refer to any surrounding environment, whether in vivo or in vitro, e.g. gastric fluid or any liquid, such as a solvent or an aqueous solution or suspension.

The present invention provides an oral pharmaceutical composition in unit dosage form comprising a drug, a pH-dependent agent, and a pH-independent agent.

The term "unit dosage form" refers to intact (i.e., not physically compromised) physically discrete units suitable as unitary dosages for administration to a subject. Examples of unit dosage forms include, but are no limited to tablets, capsules, microtablets, granules, pellets, lollipops, and lozenges. In preferred embodiments, the unit dosage form comprises a tablet.

The pharmaceutical composition may be formulated for immediate release or extended release characteristics. The term "extended release" is used to refer to a composition which is formulated to provide for the gradual release of an drug over an extended period of time, preferably over 2 to 48 hours, more preferably over 4 to 36 hours, and most preferably over 6 to 24 hours. The term "extended release" includes controlled release and delayed release and may optionally contain an immediate release component. In some embodiments of the present invention containing an extended release portion, preferably <25%, more preferably <20%, of the drug is released in the first hour from the composition; preferably 15-50%, more preferably 20-45%, of the drug is released in the first two (2) hours from the composition; preferably 40-80%, more preferably 45-75%, of the drug is released in the first four (4) hours from the composition; and preferably >75%, more preferably >80%, of the drug is released after eight (8) hours from the composition. In some other embodiments of the present invention containing an extended release portion, preferably about 5% to about 25% of the drug is released after 1 hour, from about 40% to about 75% of the drug is released after 8 hours, and not less than 80% is released after 18 hours. In some alternative embodiments of the present invention containing an extended release portion, preferably about 10% to about 30% of the drug is released after 2 hours, from about 40% to about 70% of the drug is released after 8 hours, and at least about 80% of the drug is released after 22 hours. In some embodiments, the pharmaceutical composition is formulated for immediate release. The term "immediate release" is used to refer to a pharmaceutical composition which is formulated to release about 80% or more of an drug after 4 hours, more preferably after 2 hours, and most preferably after 1 hour after oral administration. In preferred embodiments, the pharmaceutical composition is formulated to release about 80% or more, more preferably about 90% or more, even more preferably about 95% of the drug in the pharmaceutical composition after about 1 hour after oral administration of the unit dosage form (for example, after swallowing the tablet or capsule or other dosage form).

The term "pH-dependent agent" refers to a component which is affected by the pH of the surrounding environment. In particular, the pH-dependent agent may be a compound, such as a polymer, whose characteristics, such as chemical and/or physical properties, vary according to the pH of the surrounding environment. The surrounding environment could comprise any type of liquid medium, such as gastric fluid. In some embodiments wherein the pharmaceutical composition is orally administered to a subject, the surrounding liquid may comprise gastric fluid. In some other embodiments, the surrounding liquid may be an in vitro bath, such as water, an acidic or an alkaline solution. In some embodiments, the pH-dependent agent is affected by (i.e., dissolves when exposed to) a decrease in pH. In some embodiments, the pH-dependent agent is affected when the pH is below about 6, preferably below 5, more preferably below 4, even more preferably below 3. In some embodiments, the characteristics of the pH-dependent agent may be affected to a greater degree at different pHs. For example, the pH-dependent agent's physical or chemical characteristics may be affected to a greater degree at a pH of 4 or lower, compared to at a pH of 5.

The pH-dependent agent may comprise a compound such as a pharmaceutical excipient. In some embodiments, the pH-dependent agent comprises a pH-dependent polymer. Examples of pH-dependent polymers include, but are not limited to certain methacrylate-based polymers, such as cationic polymers with a dimethylaminoethyl ammonium group. These polymers are marketed under trade names such as EUDRAGIT® E 100, and EUDRAGIT® E PO. In preferred embodiments, the pH-dependent polymer comprises EUDRAGIT® E100, or poly(butyl methacrylate-co-(2-demethylaminoeethyl) methacrylate-co-methyl methacrylate), 1:2:1. EUDRAGIT® E100 is a cationic polymer with dimethylaminoethyl methacrylate as a functional group (CAS Registry No. 24938-16-7).

The "pH-independent agent" refers to a component whose characteristics do not generally vary according to the pH of the surrounding environment. In particular, the pH-independent agent may be a compound, such as a polymer, whose characteristics, such as chemical and/or physical properties, do not vary significantly with changes in the pH of the surrounding environment. The pH-independent agent may comprise a compound such as a pharmaceutical excipient. In some embodiments, the pH-independent agent comprises a pH-independent polymer. Examples of pH-independent agents include cellulose-type agents, including but not limited to hydroxyethyl cellulose polymers, ethylcellulose polymers, methylcellulose polymers, and hydroxypropyl methylcellulose polymers; and certain methacrylate-based polymers, including but not limited to methacrylate/acrylate copolymers with trimethyl-ammonioethyl-amethacylate as a functional group, and neutral polymers of methacrylate/acrylates. Cellulose-type agents are marketed under trade names such as ETHOCEL® and METHOCEL®, which include a number of subtypes based on physical/chemical properties. Examples of pH-independent methacrylate-based polymers include those marketed under trade names such as EUDRAGIT® RL 30D, EUDRAGIT® RL PO, EUDRAGIT® RL 100, EUDRAGIT® RL 12, 5, EUDRAGIT® RS 30D, EUDRAGIT® RS PO, EUDRAGIT® RS 100, EUDRAGIT® RS 12,5, EUDRAGIT® NE 30D, EUDRAGIT® NE 40D, and EUDRAGIT® NM 30D. In some preferred embodiments, the pH-independent agent comprises an ethylcellulose polymer, such as those marketed under the trade name ETHOCEL®. In preferred embodiments, the pH-independent agent comprises ETHOCEL® 45, which is an ethylcellulose having a viscosity of about 41-49.

in some embodiments, the pharmaceutical composition may comprise a portion, part, or section which comprises both the pH-dependent agent and pH-independent agent. For example, the composition may comprise a layer or coating which comprises both the pH-dependent agent and the pH-independent agent. In some other embodiments, the pH-dependent agent and pH-independent agent may each be present in separate parts or sections (such as, separate layers) of the pharmaceutical composition. In some other embodiments, the multiple sections containing pH-dependent agent may be distributed within a section comprising the pH-independent agent, or vice versa.

In some embodiments, the composition may comprise the drug in a portion, part, or section of the pharmaceutical composition which is separate from the part(s) or section(s) of the pharmaceutical composition which comprises the pH-dependent agent and the pH-independent agent. The composition may comprise the drug in an inner portion, and the pH-dependent agent and pH-independent agent in one or more outer portions. For example, in some embodiments, the pH-dependent agent and pH-independent agent may be comprised in one or more layers or coatings which cover the portion, part, or section of the pharmaceutical composition which comprises the drug (for example, a core or layer containing the drug). In these embodiments, the layer or coating may partially or substantially cover the drug-containing portion, part, or section of the pharmaceutical composition. The term "substantially cover" means that preferably about 70% or more, more preferably about 80% or more, even more preferably about 90% or more, and most preferably about 95% or more of the part of the composition comprising the drug is covered. In some embodiments, 100% coverage is suitable.

In embodiments wherein the pH-dependent agent and pH-independent agent are comprised in one or more layers or coatings which cover the portion, part or section of the composition which comprises the drug, the drug-containing portion, part, or section may be in any form. For example, the drug-containing portion, part, or section may be a tablet core or a capsule, and the pH-dependent agent and pH-independent agent may be comprised in a coating which partially or substantially covers the tablet core or capsule. In some embodiments, the active-ingredient portion, part, or section may comprise the pharmaceutical composition disclosed in U.S. Pat. No. 7,955,619, which is incorporated by reference in its entirety, and the pH-dependent agent and pH-independent agent may be comprised in one or more coatings. In some embodiments, the pharmaceutical may comprise a matrix comprising the pH-dependent agent and the pH-independent agent, and the drug is distributed within the matrix.

In some embodiments wherein the pharmaceutical composition comprises a coating or layer comprising the pH-dependent agent and the pH-independent agent and the coating or layer which covers or surrounds the part of the pharmaceutical composition comprising the active component, the release of the drug may be affected by a reduction of the dissolution of the coating or layer. For example, at a certain pH, such as at normal gastric pH, the coating or layer may dissolve substantially and then a substantial amount of the drug is released from the pharmaceutical composition. However, at another pH, for example, above pH 6, the dissolution of the coating or layer may be reduced, preferably significantly, and/or the coating or layer may remain partially or substantially intact, and the total amount of the drug is not released from the pharmaceutical composition. In some embodiments wherein the pH-dependent agent and pH-independent agents are comprised in a matrix in which the drug is distributed, a similar effect may be achieved. For example, at a certain pH, for example, at normal gastric pH, the matrix may release the total amount of drug from pharmaceutical composition. However, at another pH, for example, at about pH 6 or above, the matrix may remain substantially intact or otherwise not release the total amount of the drug from the pharmaceutical composition. In some embodiments, the reduced amount and rate of release makes it difficult for subjects to abuse the drug by injection to attain a "high," as in some cases, the pharmaceutical composition may be partially or substantially undissolved, and it is difficult to draw up a large amount of drug in a syringe.

In some embodiments, the weight ratio of pH-dependent agent:pH-independent agent present in the composition is about 50:1 to 1:50, preferably 25:1 to 1:25, and more preferably 10:1 to 1:1. In some preferred embodiments, the pH-dependent agent and pH-independent agent are comprised in the same portion, part, or section of the composition, such as in a layer or coating, and the weight ratio of pH-dependent agent:pH-independent agent is about 10:1 to 10:6, more preferably about 10:2 to 10:4, and most preferably about 10:3. In preferred embodiments, the composition comprises a cationic polymer with dimethyl-aminoethyl methacrylate as a functional group, preferably EUDRAGIT® E100 (a pH-dependent agent), and an ethylcellulose polymer, preferably ETHOCEL® 45 (a pH-independent agent), in a ratio of EUDRAGIT® E100:ETHOCEL® 45 of about 10:3.

The term "drug" includes any compound which has pharmacological or biological activity. A drug may comprise an active pharmaceutical ingredient or a salt, ester, or derivative thereof. In some embodiments, the drug include, but are not limited to analgesics, anti-inflammatory agents, anti-helminthics, anti-arrhythmic agents, anti-asthma agents, anti-bacterial agents, anti-viral agents, anti-coagulants, anti-dementia agents, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, immunosuppressants, anti-protozoal agents, anti-thyroid agents, anti-tussives, anxiolytics, sedatives, hypnotics, neuroleptics, neuroprotective agents, β-blockers, cardic inotropic agents, cell adhesion inhibitors, corticosteroids, cytokine receptor activity modulators, diuretics, anti-Parkinson's agents, gastro-intestinal agents, histamine H-receptor antagonists, keratolytics, lipid regulating agents, muscle relaxants, nitrates and other anti-anginal agents, non-steroid anti-asthma agents, nutritional agents, opioid analgesics, sex hormones, stimulants and anti-erectile dysfunction agents; and salts, esters, and mixtures thereof. In preferred embodiments, the drug is one that is often abused, such as a central nervous system stimulant or depressant. Examples of central nervous system stimulants include, but are not limited to, amphetamines and agents such as cocaine. Examples of central nervous depressants include, but are not limited to but are not limited to opioids, barbiturates, benzodiazepines, and other anxiety and sleep medications.

Stimulants increase heart rate, blood pressure and metabolism, sometimes providing feelings of exhilaration and energy and increased mental alertness. Amphetamines such as methylphenidate (sometimes marketed under the tradename RITALIN®) and dextroamphetamine (sometimes marketed under the tradenames ADDERALL® and DEXEDRINE®) are often prescribed for the treatment of narcolepsy, attention-deficit/hyperactivity disorder, and depression that has not responded to other treatments. They also may be used for short-term treatment of obesity. Individuals may become addicted to the sense of well-being and enhanced energy that stimulants can generate. Taking high doses of stimulants repeatedly over a short time, however, can lead to feelings of hostility or paranoia. Additionally, taking high doses of stimulants may result in dangerously high body temperatures and an irregular heartbeat.

Examples of opioids include, but are not limited to the following: alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, and tramadol. Any opioid or pharmaceutically acceptable salt or ester thereof may be used in the abuse deterrent composition. Preferred opioids include fentanyl, sufentanil, carfentanil, lofentanil, alfentanil, hydromorphone, oxycodone, morphine, hydroxycodone, propoxyphene, pentazocine, methadone, tilidine, butorphanol, buprenorphine, levorphanol, codeine, oxymorphone, meperidine, and dihydrocodeinone. More preferred opioids include oxycodone, hydrocodone, codeine, morphine, oxymorphone and hydromorphone, and pharmaceutically acceptable salts and esters thereof.

Examples of barbiturates include, but are not limited to mephobarbital (which is sometimes marketed under the tradename MEBARAL®) and pentobarbital sodium (which is sometimes marketed under the tradename NEMBUTAL®). Barbiturates are often prescribed to treat anxiety, tension, and sleep disorders.

Examples of benzodiazepines and benzodiazepine derivatives include, but are not limited to diazepam (sometimes marketed under the tradename VALIUM®), alprazolam (sometimes marketed under the tradename XANAX®), triazolam (HALCION®), and estazolam (PROSOM®). Benzodiazepines are often prescribed to treat anxiety, acute stress reactions, and panic attacks.

An example of another CNS depressant is zaleplon, which is sometimes marked under the tradename SONATA®.

The present invention provides for compositions comprising one or more drugs. In some embodiments, the compositions comprise one or more opioids. The present invention also provides for compositions comprising one or more opioids, wherein the compositions do not comprise an opioid antagonist or any other non-opioid agonist. The present invention provides for compositions comprising one or more drugs but not comprising any adverse agent. Adverse agents refer for agents which reduce or eliminate one or more pharmacological effects of the drug or agents which cause an undesired physiological reaction, such as emesis. Adverse agents include, but are not limited to antagonists such as opioid antagonists, mucous membrane irritants, and emetics. The present invention provides compositions which do not comprise naloxone or natrexone.

Preferred embodiments of the invention include an drug in the amounts as follows: oxycodone or a pharmaceutically acceptable salt thereof, which is present in an amount of about 5 mg to about 400 mg; morphine or a pharmaceutically acceptable salt thereof, which is present in an amount of about 15 mg to about 800 mg; hydromorphone or a pharmaceutically acceptable salt thereof, which is present in an amount of about 1 mg to about 64 mg; hydrocodone or a pharmaceutically acceptable salt thereof, which is present in an amount of about 5 mg to about 400 mg; and oxymorphone or a pharmaceutically acceptable salt thereof, which is present in an amount of about 4 mg to about 80 mg.

In some embodiments, the compositions of the present invention comprise morphine or a pharmaceutically acceptable salt thereof. Salts of morphine include, but are not limited to sulfate, sulfate pentahydrate, hydrochloride, hydrochloride trihydrate, meconate, valerate, acetate, citrate, bitartrate, stearate, phthalate, hydrobromide, hydroiodide, mucate, nitrate, salicylate, phenylpropionate, phosphate, methyliodide, isobutyrate, hypophosphite, tannate, tartrate, methylbromide, methylsulfonate, and those disclosed in EP 0137600, which is incorporated herein by reference. In preferred embodiments, the composition comprises morphine sulfate or morphine sulfate pentahydrate.

In some embodiments, the compositions of the present invention comprise oxycodone or a pharmaceutically acceptable salt thereof. Salts of oxycodone include, but are not limited to hydrochloride, hydrobromide, hydroiodide, sulfate, bisulfate, nitrate, citrate, tartrate, bitartrate, phosphate, malate, maleate, fumarate, succinate, acetate, terephthalate, and pamoate. In preferred embodiments, the composition comprises oxycodone hydrochloride.

In some embodiments, the compositions of the present invention comprise oxymorphone or a pharmaceutically acceptable salt thereof. Examples of oxymorphone include, but are not limited to hydrochloride, sulfate, nitrate, phosphate, hydrobromide, malate, maleate, ascorbate, citrate, tartarate, pamoate, laurate, stearate, palmitate, oleate, myristate, lauryl sulfate, linoleate, and linolenate. In some preferred embodiments, the composition comprises oxymorphone hydrochloride.

In some embodiments, the compositions of the present invention comprise hydrocodone or a pharmaceutically acceptable salt thereof. Salts of hydrocodone include, but are not limited to, bitartrate, bitartrate hydrate, hydrochloride, p-toluenesulfonate, phosphate, thiosemicarbazone, sulfate, trifluoroacetate, hemipentahydrate, pentafluoropropionate, p-nitrophenylhydrazone, o-methyloxime, semicarbazone, hydrobromide, mucate, oleate, phosphate dibasic, phosphate monobasic, acetate trihydrate, bis(heptafluorobutyrate), bis(methylcarbamate), bis(pentafluoropropionate), bis(pyridine carboxylate), bis(trifluoroacetate), chlorhydrate, and sulfate pentahydrate. In some preferred embodiments, the compositions of the present invention comprise hydrocodone bitartrate.

In some embodiments, the compositions of the present invention comprise hydromorphone or a pharmaceutically acceptable salt thereof. Salts of hydromorphone include, but are not limited to, sulfate, hydrochloride, sodium chloride, trifluoracetate, thiosemicarbazone hydrochloride, pentafluoropropionate, p-nitrophenyl-hydrozone, hydrazine, hydrobromide, mucate, methylbromide, oleate, n-oxide, acetate, phosphate dibasic, phosphate monobasic, acetate trihydrate, bis(heptafluorobutyrate), bis(methylcarbamate), (bis-pentafluoropropionate), bis(pyridine-3-carboxylate), bis(trifluoroacetate), bitartrate, chlorohydrate, and sulfate pentahydrate. In xsome preferred embodiments, the compositions of the present invention comprise hydromorphone hydrochloride.

The pharmaceutical composition is "physically compromised" when it is in a form other than an intact form. A pharmaceutical composition is physically compromised when the physical integrity of the pharmaceutical composition or dosage form is compromised. This can be achieved by various means such as by chopping, grinding, crushing, or placing into solvents, such as those containing alcohol (e.g., ethyl alcohol) and/or water. In preferred embodiments, the physically compromised composition is in a chopped, ground, or crushed form. A pharmaceutical composition may be physically compromised in a number of ways, including but not limited to use of a pill crusher, a pill splitter, a mortar and pestle, a solid object such as a hammer or a spoon, a sharp object such as a razor, a grinder such as a coffee bean grinder, or a blender. In some embodiments, the average particle size of the physically compromised pharmaceutical composition is less than 6 mm, alternatively less than 5 mm, alternatively less than 4 mm, alternatively less than 3 mm, alternatively less than 2 mm, alternatively less than 1 mm, alternatively less than 0.5 mm, alternatively less than 0.25 mm.

The present invention provides orally administrable pharmaceutical compositions comprising a drug and optionally comprising a pH-dependent agent and pH-independent agent. The orally administrable pharmaceutical compositions may optionally comprise a coating.

The area under the curve, or "AUC" refers to the area under the serum concentration curve, or the integral of the blood serum concentration of the drug substance over a period of time. The AUC achieved after a period of time refers to the AUC calculated after an amount of time after administration. In some embodiments, the period of time is about 30 minutes to about 24 hours after administration. In some embodiments, the period of time is selected from the group consisting of about 30 minutes, about 1 hour, about 2 hours, about 4 hours, about 8 hours, about 12 hours, and about 24 hours and the AUC is calculated at any of these time points after administration. In some preferred embodiments, the period of time is selected from the group consisting of: about 0.5 hours, 1 hour, and 2 hours. In some embodiments, the AUC may refer to the "$AUC_{0-t}$". The term "$AUC_{0-t}$" refers to the AUC from time zero ("0") to "t" wherein "t" is the last time point with measurable concentration for individual formulation. The sum of the AUC of the drug and the AUC of the major metabolite refers to the total amount of AUC of both the drug and the major metabolite, calculated at the same time point.

The present invention also provides an orally administrable pharmaceutical composition comprising a drug, wherein the composition is configured such that when the pharmaceutical composition is administered intranasally in physically compromised form to a subject, the area under the curve (AUC) of drug after a period of time is less than 200% of the AUC of the drug achieved after oral administration of an intact form of the pharmaceutical composition after the same period of time. In some embodiments, the AUC of the drug after a period of time is less than 175%, alternatively less than 150%, or alternatively less than 125% of the AUC of the drug achieved after oral administration of an intact form of the pharmaceutical composition after the same period of time.

The present invention provides an orally administrable pharmaceutical composition comprising a drug, wherein the composition is configured such that when the pharmaceutical composition is administered intranasally in physically compromised form to a subject, the area under the curve (AUC) of a major metabolite of the drug after a period of time is at least 15% of the AUC of the major metabolite achieved after oral administration of an intact form of the pharmaceutical composition after the same period of time. In some embodiments, the AUC of a major metabolite of the drug after a period of time is at least 20%, alternatively at least 25%, alternatively at least 30%, alternatively at least 35%, alternatively at least 40%, alternatively at least 45% of the AUC of the major metabolite achieved after oral administration of an intact form of the pharmaceutical composition after the same period of time.

A metabolite is a compound derived from the parent drug through Phase I and/or Phase II metabolic pathways. A major metabolite of a drug may refer to a metabolite which in the human plasma accounts for 10% of the parent drug systemic exposure or administered dose. The major metabolite may refer to active or inactive metabolites.

Preferably, when the drug is morphine, the major metabolite is selected from the group consisting of: morphine-3-glucuronide (M3G), morphine-6-glucuronide (M6G), hydromorphone, normorphine (NM) and minor metabolites such as morphine-3,6-diglucuronide, morphine-3-ethereal sulfate, normorphine-6-glucuronide, and normorphine-3-glucuronide. Preferably, when the drug is oxycodone, the major metabolite is selected from the group consisting of: noroxycodone, α oxycodol, β oxycodol, oxymorphone, α oxymorphol, β oxymorphol, noroxymorphone, α noroxycodol, β noroxycodol, noroxymorphone, 14-hydroxydihydrocodeine, and 14-hydroxydihydromorphine. Preferably, when the drug is oxymorphone, the major metabolite is selected from the group consisting of:
oxymorphone-3-glucuronide and 6-hydroxy-oxymorphone.
Preferably, when the drug is hydromorphone, the major metabolite is selected from the group consisting of: hydromorphone-3-glucuronide, hydromorphone-3-glucoside and dihydroisomorphine-6-glucuronide. Preferably, when the drug is codeine, the major metabolite is selected from the group consisting of: codeine-6-glucuronide (C6G), norcodeine, hydrocodone, morphine, morphine-3-glucuronide, morphine-6-glucuronide, and normorphine. Preferably, when the drug is methylphenidate, the major metabolite is selected from the group consisting of: ethylphenidate, ritalinic acid (α-phenyl-2-piperidine acetic acid), hydroxymethylphenidate, and hydroxyritalinic acid. Preferably, when the drug is amphetamine or dextroamphetamine, the major metabolite is selected from the group consisting of: 4-hydroxyamphetamine, benzoic acid, phenylacetone, hippuric acid, 4-hydroxynorephedrine, and norephedrine. Preferably, when the drug Is lisdexamfetamine, the major metabolite is selected from the group consisting of: phenethylamine and dextroamphetamine. Preferably, when the drug is alprazolam, the major metabolite is selected from the group consisting of 4-hydroxyalprazolam and α-hydroxyalprazolam. Preferably, when the drug is lorazepam, the major metabolite is selected from the group consisting of: 3-O-phenolic glucuronide and lorazepam glucuronide. Preferably, when the drug is diazepam, the major metabolite is seleted from the group consisting of desmethyldiazepam, esmethyldiazepam, oxazepam, and temazepam.

The present invention also provides an orally administrable pharmaceutical composition comprising a drug, wherein the composition is configured such that when the pharmaceutical composition is administered intranasally in physically compromised form to a subject, the ratio of the area under the curve (AUC) of the drug to the AUC of a major metabolite of the drug (drug:major metabolite) achieved after a period of time is less than 25 times the ratio of the AUC of the drug to the AUC of the major metabolite (drug:major metabolite) achieved after the same period of time after oral administration of the pharmaceutical composition in an intact form. The "ratio of the AUC of the drug to the AUC of a major metabolite" refers to the AUC of the drug, divided by the AUC of a major metabolite. In some embodiments, the ratio of the area under the curve (AUC) of the drug to the AUC of a major metabolite of the drug (drug:major metabolite) achieved after a period of time is less than 20 times, alternatively less than 10 times the ratio of the AUC of the drug to the AUC of the major metabolite (drug:major metabolite) achieved after the same period of time after oral administration of the pharmaceutical composition in an intact form. In some embodiments, when the AUC is the $AUC_{0-t}$, the ratio of the area under the curve (AUC) of the drug to the AUC of a major metabolite of the drug (drug:major metabolite) achieved after a period of time is less than 20 times, alternatively less than 10 times, alternatively less than 8 times, alternatively less than 5 times, alternatively less than 3 times, the ratio of the AUC of the drug to the AUC of the major metabolite (drug:major metabolite) achieved after the same period of time after oral administration of the pharmaceutical composition in an intact form. In some embodiments, when the period of time is about 0.5 hour, the ratio of the area under the curve (AUC) of the drug to the AUC of a major metabolite of the drug (drug:major metabolite) achieved after a period of time is about 1 to 10, alternatively about 2 to 8, alternatively about 4 to 7 times the ratio of the AUC of the drug to the AUC of the major metabolite (drug:major metabolite) achieved after the same period of time after oral administration of the pharmaceutical composition in an intact form. In some embodiments, when the period of time is about 1 hour, the ratio of the area under the curve (AUC) of the drug to the AUC of a major metabolite of the drug (drug:major metabolite) achieved after a period of time is about 1 to 15, alternatively about 2 to 10, alternatively about 5 to 8 times the ratio of the AUC of the drug to the AUC of the major metabolite (drug:major metabolite) achieved after the same period of time after oral administration of the pharmaceutical composition in an intact form. In some embodiments, when the period of time is about 2 hours, the ratio of the area under the curve (AUC) of the drug to the AUC of a major metabolite of the drug (drug:major metabolite) achieved after a period of time is about 1 to 10, alternatively about 2 to 8, alternatively about 3 to 6 times the ratio of the AUC of the drug to the AUC of the major metabolite (drug:major metabolite) achieved after the same period of time after oral administration of the pharmaceutical composition in an intact form.

The present invention also provides an orally administrable pharmaceutical composition comprising a drug, wherein the composition is configured such that when the pharmaceutical composition is administered intranasally in physically compromised form to a subject, the ratio of the area under the curve (AUC) of the drug to the AUC of a major metabolite of the drug (drug:major metabolite) achieved after a period of time is about 10 or less. In some embodiments, the ratio of the area under the curve (AUC) of the drug to the AUC of the major metabolite (drug:major metabolite) achieved after a period of time is about 8 or less, or alternatively about 6 or less. In some embodiments wherein the AUC is the $AUC_{0-t}$, the ratio of the area under the curve (AUC) of the drug to the AUC of the major metabolite (drug:major metabolite) achieved after a period of time is about 0.1 to about 4, alternatively about 0.2 to about 3, alternatively about 0.3 to about 1, or alternatively about 0.4 to about 0.5. In some embodiments wherein the period of time is about 0.5 hour, the ratio of the area under the curve (AUC) of the drug to the AUC of the major metabolite (drug:major metabolite) achieved after a period of time is about 1 to about 10, alternatively about 2 to about 8, or alternatively about 3 to about 6. In some embodiments wherein the period of time is about 1 hour, the ratio of the area under the curve (AUC) of the drug to the AUC of the major metabolite (drug:major metabolite) achieved after a period of time is about 1 to about 5, alternatively about 2 to about 4, or alternatively about 2 to about 3. In some embodiments wherein the period of time is about 2 hours, the ratio of the area under the curve (AUC) of the drug to the AUC of the major metabolite (drug:major metabolite) achieved after a period of time is about 0.5 to about 5, alternatively about 0.75 to about 3, or alternatively about 1 to about 2.

The present invention also provides an orally administrable pharmaceutical composition comprising a drug, wherein the composition is configured such that when the pharmaceutical composition is administered intranasally in physically compromised form to a subject, the sum of the area under the curve (AUC) of the drug and the AUC of a major metabolite of the drug after a period of time is less than the sum of the AUC of the drug and the AUC of the major metabolite achieved after the same period of time after oral administration of the pharmaceutical composition in an intact form. In some embodiments, the sum of the area under the curve (AUC) of the drug and the AUC of a major metabolite of the drug after a period of time at least 10% lower, alternatively at least 20% lower, alternatively at least 25% lower, alternatively at least 30% lower, alternatively at least 35% lower, alternatively at least 40% lower, or alternatively at least 45% lower than the sum of the AUC of the drug and the AUC of the major metabolite achieved after the same period of time after oral administration of the pharmaceutical composition in an intact form.

The present invention also provides an orally administrable pharmaceutical composition comprising 60 mg of morphine or a salt thereof, wherein the composition is configured such that when the pharmaceutical composition is administered intranasally in physically compromised form to a subject, the sum of the area under the curve (AUC) of morphine and the AUC of a major metabolite, such as morphine-6-glucuronide (M6G), after a period of time is less than 900 ng·h/mL. In some embodiments wherein the composition comprises 60 mg morphine and the AUC is the $AUC_{0-t}$, the sum of the AUC of morphine and the AUC of M6G is about 100 ng·h/mL to about 800 ng·h/mL, alternatively about 200 ng·h/mL to about 700 ng·h/mL, alternatively about 300 ng·h/mL to about 600 ng·h/mL, or alternatively about 500 ng·h/mL to about 600 ng·h/mL. In some embodiments wherein the composition comprises 60 mg morphine and the time period is about 0.5 hour, the sum of the AUC of morphine and the AUC of M6G is less than 50 ng·h/mL, alternatively about 0.5 ng·h/mL to about 25 ng·h/mL, alternatively about 1 ng·h/mL to about 10 ng·h/mL, or alternatively about 1 ng·h/mL to about 5 ng·h/mL. In some embodiments wherein the composition comprises 60 mg morphine and the time period is about 1 hour, the sum of the AUC of morphine and the AUC of M6G is less than 75 ng·h/mL, alternatively about 1 ng·h/mL to about 50 ng·h/mL, alternatively about 5 ng·h/mL to about 25 ng·h/mL, or alternatively about 10 ng·h/mL to about 20 ng·h/mL. In some embodiments wherein the composition comprises 60 mg morphine and the time period is about 2 hours, the sum of the AUC of morphine and the AUC of M6G is less than 250 ng·h/mL, alternatively about 5 ng·h/mL to about 150 ng·h/mL, alternatively about 25 ng·h/mL to about 100 ng·h/mL, or alternatively about 40 ng·h/mL to about 80 ng·h/mL.

The present invention also provides an orally administrable pharmaceutical composition comprising morphine or a salt thereof, wherein the composition is configured such that when the pharmaceutical composition is administered intranasally in physically compromised form to a subject, the sum of the area under the curve (AUC) of morphine and the AUC of a major metabolite, such as morphine-6-glucuronide (M6G), after a period of time is less than 20 ng·h/mL/mg (ng·h/mL per mg of morphine). In some embodiments wherein the composition comprises morphine and the AUC is the $AUC_{0-t}$, the sum of the AUC of morphine and the AUC of M6G is about 1 ng·h/mL/mg to about 18 ng·h/mL/mg, alternatively about 5 ng·h/mL/mg to about 15 ng·h/mL/mg, or alternatively about 8 ng·h/mL/mg to about 12 ng·h/mL/mg. In some embodiments wherein the composition comprises morphine and the time period is about 0.5 hour, the sum of the AUC of morphine and the AUC of M6G is less than 0.5 ng·h/mL/mg, alternatively about 0.01 ng·h/mL/mg to about 0.3 ng·h/mL/mg, alternatively about 0.02 ng·h/mL/mg to about 0.1 ng·h/mL/mg, or alternatively about 0.03 ng·h/mL/mg to about 0.07 ng·h/mL/mg. In some embodiments wherein the composition comprises morphine and the time period is about 1 hour, the sum of the AUC of morphine and the AUC of M6G is less than 1 ng·h/mL/mg, alternatively about 0.05 ng·h/mL/mg to about 0.75 ng·h/mL/mg, alternatively about 0.1 ng·h/mL/mg to about 0.5 ng·h/mL/mg, or alternatively about 0.15 ng·h/mL/mg to about 0.35 ng·h/mL/mg. In some embodiments wherein the composition comprises morphine and the time period is about 2 hours, the sum of the AUC of morphine and the AUC of M6G is less than 5 ng·h/mL/mg, alternatively about 0.1 ng·h/mL/mg to about 2.5 ng·h/mL/mg, alternatively about 0.5 ng·h/mL/mg to about 2 ng·h/mL/mg, or alternatively about 0.75 ng·h/mL/mg to about 1.5 ng·h/mL/mg.

The present invention also provides an orally administrable pharmaceutical composition comprising 60 mg of morphine or a salt thereof, wherein the composition is configured such that when the pharmaceutical composition is administered intranasally in physically compromised form to a subject, the area under the curve (AUC) of the morphine after a period of time is less than 400 ng·h/mL. In some embodiments wherein the composition comprises 60 mg morphine and the AUC is the $AUC_{0-t}$, the AUC of morphine is about 50 ng·h/mL to about 300 ng·h/mL, alternatively about 100 ng·h/mL to about 200 ng·h/mL, or alternatively about 125 ng·h/mL to about 175 ng·h/mL. In some embodiments wherein the composition comprises 60 mg morphine and the time period is about 0.5 hour, the AUC of morphine is less than 10 ng·h/mL, alternatively about 0.5 ng·h/mL to about 8 ng·h/mL, alternatively about 1 ng·h/mL to about 5 ng·h/mL, or alternatively about 2 ng·h/mL to about 3 ng·h/mL. In some embodiments wherein the composition comprises 60 mg morphine and the time period is about 1 hour, the AUC of morphine is less than 50 ng·h/mL, alternatively about 2.5 ng·h/mL to about 25 ng·h/mL, alternatively about 5 ng·h/mL to about 15 ng·h/mL, or alternatively about 8 ng·h/mL to about 12 ng·h/mL. In some embodiments wherein the composition comprises 60 mg morphine and the time period is about 2 hours, the AUC of morphine is less than 100 ng·h/mL, alternatively about 5 ng·h/mL to about 75 ng·h/mL, alternatively about 10 ng·h/mL to about 50 ng·h/mL, or alternatively about 25 ng·h/mL to about 35 ng·h/mL.

The present invention also provides an orally administrable pharmaceutical composition comprising morphine or a salt thereof, wherein the composition is configured such that when the pharmaceutical composition is administered intranasally in physically compromised form to a subject, the area under the curve (AUC) of morphine after a period of time is less than 10 ng·h/mL/mg (ng·h/mL per mg of morphine). In some embodiments wherein the composition comprises morphine and the AUC is the $AUC_{0-t}$, the AUC of morphine is about 1 ng·h/mL/mg to about 8 ng·h/mL/mg, alternatively about 2 ng·h/mL/mg to about 6 ng·h/mL/mg, or alternatively about 3 ng·h/mL/mg to about 4 ng·h/mL/mg. In some embodiments wherein the composition comprises morphine and the time period is about 0.5 hour, the AUC of morphine is less than 0.5 ng·h/mL/mg, alternatively about 0.01 ng·h/mL/mg to about 0.2 ng·h/mL/mg, alternatively about 0.02 ng·h/mL/mg to about 0.1 ng·h/mL/mg, or alternatively about 0.03 ng·h/mL/mg to about 0.05 ng·h/mL/mg. In some embodiments wherein the composition comprises morphine and the time period is about 1 hour, the AUC of morphine is less than 1 ng·h/mL/mg, alternatively about 0.05 ng·h/mL/mg to about 0.75 ng·h/mL/mg, alternatively about 0.1 ng·h/mL/mg to about 0.5 ng·h/mL/mg, or alternatively about 0.15 ng·h/mL/mg to about 0.25 ng·h/mL/mg. In some embodiments wherein the composition comprises morphine and the time period is about 2 hours, the AUC of morphine is less than 2.5 ng·h/mL/mg, alternatively about 0.1 ng·h/mL/mg to about 2 ng·h/mL/mg, alternatively about 0.2 ng·h/mL/mg to about 1 ng·h/mL/mg, or alternatively about 0.3 ng·h/mL/mg to about 0.75 ng·h/mL/mg.

The present invention also provides an orally administrable pharmaceutical composition comprising 60 mg of morphine or a salt thereof, wherein the composition is configured such that when the pharmaceutical composition is administered intranasally in physically compromised form to a subject, the area under the curve (AUC) of a major metabolite such as morphine-6-glucuronide (M6G) after a period of time is at least 100 ng·h/mL. In some embodiments wherein the composition comprises 60 mg morphine and the AUC is the $AUC_{0-t}$, the AUC of M6G is about 150 ng·h/mL to about 750 ng·h/mL, alternatively about 200 ng·h/mL to about 500 ng·h/mL, or alternatively about 300 ng·h/mL to about 400 ng·h/mL. In some embodiments wherein the composition comprises 60 mg morphine and the time period is about 0.5 hour, the AUC of M6G is at least about 0.1 ng·h/mL, alternatively about 0.2 ng·h/mL to about 5 ng·h/mL, alternatively about 0.3 ng·h/mL to about 1 ng·h/mL, or alternatively about 0.4 ng·h/mL to about 0.75 ng·h/mL. In some embodiments wherein the composition comprises 60 mg morphine and the time period is about 1 hour, the AUC of M6G is at least about 0.5 ng·h/mL, alternatively about 1 ng·h/mL to about 15 ng·h/mL, alternatively about 1.5 ng·h/mL to about 5 ng·h/mL, or alternatively about 0.4 ng·h/mL to about 0.75 ng·h/mL. In some embodiments wherein the composition comprises 60 mg morphine and the time period is about 2 hours, the AUC of M6G is at least about 5 ng·h/mL, alternatively about 10 ng·h/mL to about 75 ng·h/mL, alternatively about 15 ng·h/mL to about 50 ng·h/mL, or alternatively about 20 ng·h/mL to about 40 ng·h/mL.

The present invention also provides an orally administrable pharmaceutical composition comprising morphine or a salt thereof, wherein the composition is configured such that when the pharmaceutical composition is administered intranasally in physically compromised form to a subject, the area under the curve (AUC) of a major metabolite such as morphine-6-glucuronide (M6G) after a period of time is at least about 0.5 ng·h/mL/mg (ng·h/mL per mg of morphine). In some embodiments wherein the composition comprises morphine and the AUC is the $AUC_{0-t}$, the AUC of M6G is about 1 ng·h/mL/mg to about 20 ng·h/mL/mg, alternatively about 2.5 ng·h/mL/mg to about 15 ng·h/mL/mg, or alternatively about 5 ng·h/mL/mg to about 10 ng·h/mL/mg. In some embodiments wherein the composition comprises morphine and the time period is about 0.5 hour, the AUC of M6G is at least about 0.005 ng·h/mL/mg, alternatively about 0.006 ng·h/mL/mg to about 1 ng·h/mL/mg, alternatively about 0.008 ng·h/mL/mg to about 0.5 ng·h/mL/mg, or alternatively about 0.01 ng·h/mL/mg to about 0.25 ng·h/mL/mg. In some embodiments wherein the composition comprises morphine and the time period is about 1 hour, the AUC of M6G is at least about 0.01 ng·h/mL/mg, alternatively about 0.02 ng·h/mL/mg to about 1 ng·h/mL/mg, alternatively about 0.03 ng·h/mL/mg to about 0.5 ng·h/mL/mg, or alternatively about 0.05 ng·h/mL/mg to about 0.1 ng·h/mL/mg. In some embodiments wherein the composition comprises morphine and the time period is about 2 hours, the AUC of morphine is at least about 0.1 ng·h/mL/mg, alternatively about 0.2 ng·h/mL/mg to about 5 ng·h/mL/mg, alternatively about 0.25 ng·h/mL/mg to about 1 ng·h/mL/mg, or alternatively about 0.4 ng·h/mL/mg to about 0.75 ng·h/mL/mg.

The present invention further provides for a plurality of particles which may optionally comprise a pH-dependent agent and pH-independent agent and/or may optionally provide the above-described pharmacokinetic effects.

The present invention also provides a plurality of particles having a particle size distribution (D50) of about 100 μm to about 1000 μm, wherein the particles each comprise a drug and one or more pharmaceutically acceptable excipients and wherein the particles are configured such that the amount of drug released from the plurality of particles is no greater than 500% of the amount of drug released from an intact unit dosage form comprising the same amount (w/w) as the plurality of particles, under the following identical conditions: 30 mL of ethanol, 25° C., agitated at 100 rpm for a period of time.

The present invention also provides a plurality of particles having a particle size distribution (D50) of about 100 μm to about 1000 μm, wherein the particles each comprise a drug and one or more pharmaceutically acceptable excipients and wherein the particles are configured such that the rate of drug released from the plurality of particles is no greater than 500% of the rate of drug released from an intact unit dosage form comprising the same amount (w/w) as the plurality of particles, under the following identical conditions: 30 mL of ethanol, 25° C., agitated at 100 rpm for a period of time.

The present invention also provides a plurality of particles comprising: an active layer comprising a drug and a first polymer, and a barrier layer comprising a second polymer, wherein the active layer and barrier layer are bonded, and wherein the particles are configured such that the amount of drug released from the plurality of particles is no greater than 500% of the amount of drug released an intact unit dosage form comprising the same amount (w/w) as the plurality of particles, under the following identical conditions: 30 mL of ethanol, 25° C., agitated at 100 rpm for a period of time.

The present invention also provides a plurality of particles comprising: an active layer comprising a drug and a first polymer, and a barrier layer comprising a second polymer, wherein the active layer and barrier layer are bonded, and wherein the particles are configured such that the rate of drug released from the plurality of particles is no greater than 500% of the rate of drug released from an intact unit dosage form comprising the same amount (w/w) as the plurality of particles, under the following identical conditions: 30 mL of ethanol, 25° C., agitated at 100 rpm for a period of time.

The agitation may be performed with any agitator, preferably a USP Type I basket or a Type II paddle.

In some embodiments, the period of time of agitation is about 15 minutes to about 300 minutes. In some embodiments, the period of time is about 30 minutes or about 240 minutes. In some embodiments, the ethanol may be 5% ethanol, 10% ethanol, 20% ethanol, or 40% ethanol. In some embodiments, the amount of drug released and/or the rate of drug released from the plurality of particles is about 500% or less of the amount of drug released and/or the rate of drug released from an intact unit dosage form comprising the same amount (w/w) of the plurality of particles. The same amount may refer to total weight of the plurality of particles or the total amount of drug. In some embodiments, the amount or rate is about 50% to about 500%, alternatively about 100% to about 400%, alternatively about 125% to about 300%, or alternatively about 125% to about 200%.

In some embodiments, when the plurality of particles is subjected to 30 mL of 5% ethanol, agitated at 100 rpm for 30 minutes, the amount of drug released and/or the rate of drug released from the plurality of particles is about 75% to about 300%, alternatively about 100% to about 200%, alternatively about 125% to about 175% of the amount of drug released and/or the rate of drug released from an intact unit dosage form comprising the same amount (w/w) of the plurality of particles. In some embodiments, when the plurality of particles is subjected to 30 mL of 5% ethanol, agitated at 100 rpm for 240 minutes, the amount of drug released and/or the rate of drug released from the plurality of particles is about 75% to about 300%, alternatively about 100% to about 200%, alternatively about 125% to about 175% of the amount of drug released and/or the rate of drug released from an intact unit dosage form comprising the same amount (w/w) of the plurality of particles. In some embodiments, when the plurality of particles is subjected to 30 mL of 10% ethanol, agitated at 100 rpm for 30 minutes, the amount of drug released and/or the rate of drug released from the plurality of particles is about 75% to about 500%, alternatively about 100% to about 400%, alternatively about 200% to about 350% of the amount of drug released and/or the rate of drug released from an intact unit dosage form comprising the same amount (w/w) of the plurality of particles. In some embodiments, when the plurality of particles is subjected to 30 mL of 10% ethanol, agitated at 100 rpm for 240 minutes, the amount of drug released and/or the rate of drug released from the plurality of particles is about 75% to about 400%, alternatively about 100% to about 300%, alternatively about 125% to about 250% of the amount of drug released and/or the rate of drug released from an intact unit dosage form comprising the same amount (w/w) of the plurality of particles. In some embodiments, when the plurality of particles is subjected to 30 mL of 20% ethanol, agitated at 100 rpm for 30 minutes, the amount of drug released and/or the rate of drug released from the plurality of particles is about 100% to about 500%, alternatively about 200% to about 450%, alternatively about 300% to about 450% of the amount of drug released and/or the rate of drug released from an intact unit dosage form comprising the same amount (w/w) of the plurality of particles. In some embodiments, when the plurality of particles is subjected to 30 mL of 20% ethanol, agitated at 100 rpm for 240 minutes, the amount of drug released and/or the rate of drug released from the plurality of particles is about 100% to about 400%, alternatively about 150% to about 350%, alternatively about 200% to about 300% of the amount of drug released and/or the rate of drug released from an intact unit dosage form comprising the same amount (w/w) of the plurality of particles. In some embodiments, when the plurality of particles is subjected to 30 mL of 40% ethanol, agitated at 100 rpm for 30 minutes, the amount of drug released and/or the rate of drug released from the plurality of particles is about 75% to about 300%, alternatively about 100% to about 200%, alternatively about 125% to about 175% of the amount of drug released and/or the rate of drug released from an intact unit dosage form comprising the same amount (w/w) of the plurality of particles. In some embodiments, when the plurality of particles is subjected to 30 mL of 40% ethanol, agitated at 100 rpm for 240 minutes, the amount of drug released and/or the rate of drug released from the plurality of particles is about 100% to about 500%, alternatively about 250% to about 450%, alternatively about 350% to about 450% of the amount of drug released and/or the rate of drug released from an intact unit dosage form comprising the same amount (w/w) of the plurality of particles.

In some embodiments, the plurality of particles has a particle size distribution (D50) of about 100 µm to about 1000 µm. Particle size distribution (D50) is also known as the median diameter or medium value of the particle size distribution, and it refers to the value of the particle diameter at 50% in the cumulative distribution. In some embodiments, the plurality of particles comprises a D50 of about 100 µm to about 1000 µm, alternatively about 250 µm to about 750 µm, alternatively about 400 µm to about 600 µm.

In some embodiments, the present invention comprises a plurality of particles comprising: an active layer comprising a drug and a first polymer, and a barrier layer comprising a second polymer. The active layer may comprise one drug or a combination of two or more drugs. In some embodiments, the active layer comprises a drug which is substantially homogeneously distributed in the first polymer. "Substantially homogenously distributed" means that more than 80%, more preferably more than 90%, and most preferably more than 95% of the drug(s) is homogeneously distributed. In some embodiments, the first polymer comprises a diffusion polymer. Examples of diffusion polymers include, but are not limited to: a quaternary ammonium acrylic or methacrylic polymers, an acrylic or a methacrylic ester copolymers or a mixture thereof, which can also be used as sustained release agents. Common tradenames include various grades of EUDRAGIT®s (all from Röhm), and SURELEASE® (from COLORCON®). The preferred polymers of the diffusion layer are acrylic or methacrylic polymers and particularly ethyl acrylate or methyl methylacrylate dispersions. Additional examples of first polymer include, but are not limited to: cellulose, chitin, collagen, nylon, poly(alkylcyanoacrylate), polyethylene, poly(ethylene-co-vinyl acetate), poly(hydroxyethyl methacrylate), poly(hydroxypropylethyl methacrylate), poly(methyl methacrylate), poly(vinyl alcohol-co-methacrylate), poly(vinyl chloride), polyisobutene, polyurethane, and silicone rubber. In some embodiments, the active layer may comprise the first polymer and one or more additional polymers.

The barrier layer comprises a second polymer. In some preferred embodiments, the barrier layer does not comprise a drug. However, in some embodiments, the barrier layer may comprise one or more drugs. In some preferred embodiments, the second polymer and the first polymer are the same polymers. In some alternative embodiments, the second polymer differs from the first polymer. In some embodiments, the second polymer comprises polyacrylates and the copolymers thereof (such as those marked under the tradename EUDRAGIT® NE 30 D), EUDRAGIT® FS 30 D, EUDRAGIT® RS 30 D, SURELEASE® from COLORCON®, AQUACOAT® from FMC®, and mixtures of EUDRAGIT® NE 30 D and AQUACOAT®, polyethylene glycol, polyethylene oxides, polyethylenes, polypropylenes, polyvinyl chlorides, polycarbonates, polystyrenes, and the like. The preferred polymers of the barrier layer are polyacrylate and polyethylene glycol and in particular, a polyacrylate dispersion. In some embodiments, the second polymer of the barrier layer does not substantially dissolve in the gastrointestinal tract, mucous membranes, blood vessels or lungs and may pass through the body in a substantially undissolved form. "Substantially undissolved" means that less than 30%, more preferably less than 20%, and most preferably less than 10% of the polymer is dissolved.

In some preferred embodiments, the active layer and barrier layer are bonded. The bonding of the active layer and barrier layer may contribute to the abuse deterrent effect. The active layer and barrier layer may be bonded by any method known in the art, including but not limited to physical or chemical bonding. In some embodiments, the active layer and barrier layer may be physically bonded and the bond may be facilitated by the use of a tablet press or heat curing and choice of polymers. In some embodiments, the active layer and barrier layer comprise the same polymer, and the layers are heat cured or pressed together with a tablet press. In preferred embodiments, the active layer and barrier layer are bonded in a manner such that the relative surface area of the active layer increases only marginally, for example, no more than about 50%, preferably no more than about 25%, most preferably no more than about 10%, when particles comprising the active layer and barrier layer are subjected to physical compromise, for example, grinding in a mortar and pestle, pill crusher, or spoon for 300 seconds.

In some embodiments, the plurality of particles comprises the above-described active layer and barrier layer, and additionally or alternatively has the above-described particle size distribution (D50) of 100 μm to about 1000 μm.

The present invention also provides for pharmaceutical compositions in unit dosage form comprising the plurality of particles. In some embodiments, the pharmaceutical composition comprises a monolithic unit dosage form such as a tablet comprising the plurality of particles. The monolithic unit dosage form may be produced by any known method in the art, for example, by compressing the plurality of particles in a tablet press.

In some embodiments, the pharmaceutical composition comprises a tablet comprising one or more layers. In some embodiments, the composition comprises a layer comprising a drug and one or more hydrophobic polymers. In some embodiments, the hydrophobic polymers comprise polyacrylates and the copolymers thereof (such as those marked under the tradename EUDRAGIT® NE 30 D, SURELEASE® from COLORCON®, AQUACOAT® from FMC®, and mixtures of EUDRAGIT® NE 30 D and AQUACOAT®), polyethylene glycol, polyethylene oxides, polyethylenes, polypropylenes, polyvinyl chlorides, polycarbonates, polystyrenes, and the like. In some embodiments, the composition comprises polyacrylate and polyethylene glycol and in particular, a polyacrylate dispersion. In some embodiments, the pharmaceutical composition further comprises a layer comprising a hydrophilic polymer or a polymer which, when contacted with a liquid, absorbs at least a portion of the liquid and forms a gel.

The pharmaceutical composition may optionally contain sustained or extended release and/or enteric coating. Examples of such materials are cellulose acetate phthalate, hydroxypropyl methylcellulose phthalate, polyvinyl acetate phthalate, methacrylic acid:acrylic ester copolymer, hydroxypropyl methylcellulose acetate succinate, shellac, cellulose acetate trimellitate, and mixtures thereof. The pharmaceutical composition may also contain water-soluble polymers such as polyvinylpyrrolidone, hydroxypropyl cellulose, hydroxypropyl methylcellulose, polyethylene glycol having a molecular weight of from 1,700 to 20,000 and polyvinyl alcohol and monomers therefor and mixtures thereof. The use of sustained, extended and enteric coating materials is generally known in the pharmaceutical arts, and as would be understood to one skilled in the art, any suitable sustained, extended and enteric coating materials or similar agents may be used in conjunction with the present invention and embodiments thereof.

Other components may be added to any or all of the various layers provided that they do not interfere with the drug and provide a desired benefit to the pharmaceutical. Exemplary of such other components are:plasticizers, anti-adhesive, inert fillers, lipophilic agents and pigments used in a known manner. Tackiness of the water-dispersible film forming substance may be overcome by simply incorporating an anti-adhesive in the coating. Examples of anti-adhesive are metallic stearates, microcrystalline cellulose, calcium phosphate, and talc. Those of ordinary skill in the art would understand the need for and applicability of such other components to overcome manufacturing, shelf-life or release profile issues.

The pharmaceutical composition of the present invention may also further comprise one or more pharmaceutically acceptable excipients including, but are not limited to, the following:plasticizers, anti-adhesives, fillers/diluents/binders, disintegrants, glidants and lubricants, surfactants, colorants, flavoring agents, pH adjusting agents, solubilizing agents, wetting agents, solvent resistant agents and buffering agents. Other suitable pharmaceutically acceptable excipients are described in *Remington: The Science and Practice of Pharmacy*, Lippincott Williams and Wilkins, Baltimore, Md. (1995), incorporated herein by reference.

Examples of plasticizers include, but are not limited to, triacetin, acetylated monoglyceride, olive oil, acetyl tributyl citrate, acetyl triethyl citrate, glycerin, sorbitol, polyethylene glycol, and polypropyleneglycol.

Examples of anti-adhesives include, but are not limited to, metallic stearates, microcrystalline cellulose, calcium phosphate, AEROSIL® 200, and talc. Those of ordinary skill in the art would understand the need for and applicability of such other components to overcome manufacturing, shelf-life or release profile issues.

Examples of fillers/diluents/binders include, but are not limited to, sucrose, sorbitol, mannitol, various grades of lactose, various grades of microcrystalline cellulose, dextrins, maltodextrins, starches or modified starches, sodium phosphate, calcium phosphate, calcium carbonate, gelatin, polyvinylpyrrolidone, and sodium carboxymethylcellulose.

Examples of disintegrants include, but are not limited to, cellulose derivatives, including microcrystalline cellulose, low-substituted hydroxypropyl cellulose, croscarmellose sodium, alginic acid, insoluble polyvinlypyrrolidone, and sodium carboxymethyl starch.

Examples of glidants and lubricants may be incorporated such as stearic acid, metallic stearates, talc, waxes, and glycerides with high melting temperatures, colloidal silica, sodium stearyl fumarate, polyethyleneglycols, and alkyl sulphates.

Examples of surfactants include, but are not limited to, non-ionic surfactants (such as various grades of polysorbate); anionic surfactants (such as docusate sodium and sodium lauryl sulfate), and cationic surfactants (such as benzalkonium chloride). An example of an amphoteric surfactant is 1,2-diacyl-L-phosphatidylcholine.

Other appropriate pharmaceutically acceptable excipients may include colorants, flavoring agents, pH adjusting agents, solubilizing agents, wetting agents, solvent resistant agents and buffering agents.

The present invention also provides methods of making the pharmaceutical composition of the present invention. In some embodiments, the method may comprise forming a core or layer comprising a drug, and applying a coating comprising pH-dependent agent and a pH-independent agent to the core or layer. The coating may be applied by any conventional technique, including, but not limited to, pan coating, fluid bed coating or spray coating. The coating may be applied, for example, as a solution, suspension, spray, dust or powder. In preferred embodiments, the one or more coatings are applied by spray coating.

The present invention also provides methods of treating or reducing the symptoms associated with a medical condition, comprising administering to a subject in need thereof the pharmaceutical composition of the present invention. In some embodiments, the medical condition is a disease, disorder, illness, medical state, syndrome, or morbidity which would be improved, alleviated, treated, cured, or ameliorated by the administration of drug.

EXAMPLES

Example 1

The following formulations were tested:

|  | mg/tab (approximate amounts) | | |
|---|---|---|---|
| Ingredient | Test A | Test B | Present in |
| Binder(s) | 300 | 300 | Tablet Core |
| Filler(s) | 50 | 50 | Tablet Core |
| Glidant | 5 | 5 | Tablet Core |
| Lubricant | 10 | 10 | Tablet Core |
| Eudragit NE 30D | 67 | 67 | $1^{st}$ Coating |
| Filler | 25 | 25 | $1^{st}$ Coating |
| Surfactant | 0.25 | 0.25 | $1^{st}$ Coating |
| Glidant | 5 | 5 | $1^{st}$ Coating |
| Eudragit NE30D | 12.5 | 12.5 | $2^{nd}$ Coating |
| Eudragit NM30D | 12.5 | 12.5 | $2^{nd}$ Coating |
| Oxycodone hydrochloride | 30 | 30 | $2^{nd}$ Coating |
| Surfactant | 1 | 1 | $2^{nd}$ Coating |
| Glidant | 2 | 2 | $2^{nd}$ Coating |
| EUDRAGIT® E100 | 10 |  | $3^{rd}$ Coating |
| ETHOCEL® 45 (ethylcellulose) | 3 |  | $3^{rd}$ Coating |
| Plasticizer | 2 |  | $3^{rd}$ Coating |
| Lubricant | 5 |  | $3^{rd}$ Coating |
| Opadry II film-coating | 10 | 10 | $4^{th}$ Coating |
| TOTAL TABLET WEIGHT | about 550 mg | about 530 mg |  |

The following tables show the dissolution profile of TEST A tablets, which are tablets of the present invention; TEST B tablets and ROXICODONE® tablets, which are comparative tablets.

TABLE 1 shows the dissolution profile in acidic conditions (0.1N Hydrochloric acid).

TABLE 1

Comparative Dissolution Profile in 0.1N Hydrochloride acid; 500 mL; Paddles, 50 rpm
TEST A tablets, TEST B tablets, vs. ROXICODONE® (immediate release oxycodone) 30 mg tablets

| Time (minutes) | TEST A | TEST B | ROXICODONE® |
|---|---|---|---|
| 5 | 21 | 55 | 32 |
| 10 | 64 | 88 | 62 |
| 15 | 92 | 103 | 92 |
| 30 | 99 | 106 | 100 |
| 45 | 100 | 106 | 102 |
| 60 | 101 | 107 | 103 |

TABLE 2 shows the dissolution profile in neutral pH conditions (deionized water).

TABLE 2

Comparative Dissolution Profile in DI Water; 500 mL; Paddles, 50 rpm
TEST A tablets, TEST B tablets, vs. ROXICODONE® (immediate release oxycodone) 30 mg tablets

| Time (minutes) | TEST A | TEST B | ROXICODONE® |
|---|---|---|---|
| 5 | 0.1 | 62 | 59 |
| 10 | 0.3 | 92 | 81 |
| 15 | 0.6 | 98 | 88 |
| 30 | 1.4 | 99 | 92 |
| 45 | 2.9 | 100 | 98 |
| 60 | 4.6 | 100 | 100 |

Example 2

The following coating formulations were tested, both in acidic medium (HCl) and neutral pH medium (deionized water):

|  | Amount in mg | | | | | |
|---|---|---|---|---|---|---|
| Ingredients | Coating 1 | Coating 2 | Coating 3 | Coating 4 | Coating 5 | Coating 6 |
| EUDRAGIT® E100 | 10.0 | 20.0 | 10.0 | 10.0 | 0.0 | 10.0 |
| DBS | 1.5 | 3.0 | 1.5 | 1.5 | 1.5 | 1.5 |
| Magnesium Stearate | 3.5 | 7.0 | 3.5 | 3.5 | 3.5 | 3.5 |
| ETHOCEL® 45 | 0.0 | 0.0 | 2.0 | 3.0 | 3.0 | 5.0 |
| *Ethanol | 135 | 270 | 153 | 162 | 72 | 180 |
| Total weight gain | 15.0 | 30.0 | 17.0 | 18.0 | 8.0 | 20.0 |
| Release in HCl | Acceptable | Acceptable | Acceptable | Acceptable | Acceptable | Not acceptable; NLT 75% required after 45 minutes |
| Release In DI Water | Very fast; not acceptable | Very fast; not acceptable | Release more than 10% after 60 minutes; not acceptable | Acceptable | Very fast; not acceptable | Acceptable |

*Evaporated during the process

Dissolution data for the above examples in 0.1N HCl and DI Water

% Released for the above examples in 0.1N HCl and DI Water

| Time (min) | Coating 1 HCl | Coating 1 Water | Coating 2 HCl | Coating 2 Water | Coating 3 HCl | Coating 3 Water | Coating 4 HCl | Coating 4 Water | Coating 5 HCl | Coating 5 Water | Coating 6 HCl | Coating 6 Water |
|---|---|---|---|---|---|---|---|---|---|---|---|---|
| 5 | 49 | 40 | 57 | 58 | 53 | 2 | 21 | 0 | 50 | 51 | 2 | 0 |
| 10 | 75 | 69 | 79 | 75 | 83 | 4 | 64 | 1 | 76 | 75 | 13 | 0 |
| 15 | 91 | 84 | 92 | 92 | 99 | 8 | 92 | 2 | 91 | 89 | 26 | 0 |
| 30 | 98 | 95 | 97 | 95 | 101 | 18 | 99 | 2 | 95 | 95 | 38 | 1 |
| 45 | 99 | 98 | 99 | 98 | 102 | 26 | 100 | 3 | 96 | 98 | 51 | 1 |
| 60 | 101 | 102 | 100 | 101 | 102 | 35 | 101 | 4 | 98 | 100 | 68 | 2 |

Example 3

The following study was conducted to determine the relative bioavailability and abuse potential of equivalent doses of a crushed and intact formulation. The study was a randomized, double-blind study, wherein 26 subjects were tested. The following formulation was tested:

An extended release tablet formulation of the present invention containing 60 mg of morphine sulfate pentahydrate was tested.

The following mean exposures ($AUC_{0-t}$) were observed after oral administration of a 60 mg intact tablet and intranasal administration of a ground 60 mg tablet.

| | MORPHINE AUC (ng · h/mL) | | M6G AUC (ng · h/mL) | |
|---|---|---|---|---|
| | intranasal administration of ground tablet | oral administration of intact tablet | intranasal administration of ground tablet | oral administration of intact tablet |
| Cmax | 24.03 | 17.72 | 49.41 | 106.98 |
| AUC 0-t | 158.3 | 132.86 | 385.58 | 830.12 |
| AUC 0-0.5 | 2.53 | 1.76 | 0.48 | 1.84 |
| AUC 0-1 | 10.17 | 6.96 | 3.84 | 17.33 |
| AUC 0-2 | 31.4 | 21.5 | 30.89 | 95.04 |
| AUC 0-8 | 109.96 | 85.64 | 233.64 | 537.79 |
| AUC 0-12 | 130.18 | 101.14 | 294.23 | 649.01 |
| AUC 0-24 | 162.78 | 132.92 | 398.2 | 830.29 |

Example 4

The following study was conducted to determine the effect of ethanol on the amount of drug released and rate of drug release. The study compared the effect of ethanol on particles having a particle size distribution (D50) of about 425 μm, compared to the effect of ethanol on an intact tablet dosage form containing the equivalent amount of particles. Both the particles and the intact dosage forms were placed under identical conditions: 30 mL of ethanol (5%, 10%, 20%, and 40%), agitated at 100 rpm at 25° C. for either 30 minutes or 240 minutes. The results can be found in FIG. 1.

What is claimed:

1. An orally administrable pharmaceutical composition in unit dosage form comprising:
a barrier layer comprising a barrier polymer comprising a copolymer of ethyl acrylate and methyl methacrylate;
a diffusion layer covering the barrier layer and comprising a drug selected from the group consisting of oxycodone and pharmaceutically acceptable salts thereof, and a diffusion polymer comprising a copolymer of ethyl acrylate and methyl methacrylate; and
an outer coating covering the diffusion layer and comprising a pH-independent agent comprising ethyl cellulose and a pH-dependent agent comprising a cationic polymer comprising dimethylaminoethyl methacrylate, wherein the unit dosage is a tablet, wherein the outer coating does not comprise a drug, wherein the pharmaceutical composition does not comprise an opioid antagonist, mucous membrane irritant, or emetic, wherein the weight ratio of pH-dependent agent to pH-independent agent is about 10:1 to 10:6, and wherein the composition is such that when the pharmaceutical composition is administered intranasally in crushed form to a subject, a sum of the area under the curve (AUC) of the drug and the AUC of a major metabolite of the drug after a period of time is less than the sum of the AUC of the drug and the AUC of the major metabolite achieved after the same period of time after oral administration of the pharmaceutical composition in intact forms; and wherein said cationic polymer with a dimethylaminoethyl group is poly (butylmethacrylate-co-(2-dimethylaminoethyl) methacrylate co-methyl methacrylate.

2. The orally administrable pharmaceutical composition of claim 1, wherein the composition is such that when the pharmaceutical composition is administered intranasally in crushed form to a subject, the sum of the area under the curve (AUC) of the drug and the AUC of a major metabolite of the drug after a period of time is at least 10% lower than the sum of the AUC of the drug and the AUC of the major metabolite achieved after the same period of time after oral administration of the pharmaceutical composition in an intact form.

3. The orally administrable pharmaceutical composition of claim 1, wherein the composition is such that when the pharmaceutical composition is administered intranasally in crushed form to a subject, the sum of the area under the curve (AUC) of the drug and the AUC of a major metabolite of the drug after a period of time is at least 20% lower than the sum of the AUC of the drug and the AUC of the major metabolite achieved after the same period of time after oral administration of the pharmaceutical composition in intact form.

4. The orally administrable pharmaceutical composition of claim 1, wherein the period of time is selected from the group consisting of 0.5 hour, 1 hour, and 2 hours.

5. The orally administrable pharmaceutical composition of claim 1, wherein the composition is such that when the pharmaceutical composition is administered intranasally in crushed form to a subject, the sum of the $AUC_{0-t}$ of the drug and the $AUC_{0-t}$ of a major metabolite of the drug after a period of time is at least 35% lower than the sum of the $AUC_{0-t}$ of the drug and the $AUC_{0-t}$ of the major metabolite achieved after the same period of time after oral administration of the pharmaceutical composition in intact form.

6. The orally administrable pharmaceutical composition of claim 1, wherein the composition is such that when the pharmaceutical composition is administered intranasally in crushed form to a subject, the sum of the $AUC_{0-t}$ of the drug and the $AUC_{0-t}$ of a major metabolite of the drug after a period of tira e is at least 40% lower than the sum of the $AUC_{0-t}$ of the drug and the $AUC_{0-t}$ of the major metabolite achieved after the same period of time after oral administration of the pharmaceutical composition in intact form.

7. The orally administrable pharmaceutical composition of claim 1, wherein the composition is such that about 60% or more o the total amount of drug in the pharmaceutical composition is released after 60 minutes under the following dissolution conditions: 0.1 N HCl, 500 mL, USP Apparatus 2 (paddle), 50 rpm, 37° C., and wherein about 25% or less of the total amount of the drug in the pharmaceutical composition is released after 60 minutes under the following dissolution conditions: DI water, 500 mL, USP Apparatus 2 (Paddle), 50 rpm, 37° C.

8. The orally administrable pharmaceutical composition of claim 1, wherein the composition is such that no more than 50% of the total amount of drug in the pharmaceutical composition is released within 1 hour and about 50% or more of the total amount of drug in the pharmaceutical composition is released after 8 hours under the following dissolution conditons: 0.1 HCl, 500 mL, USP Apparatus 2 (paddle), 50 rpm, 37° C.; and wherein about 25% or less of the total amount of drug in the pharmaceutical composition is released after 60 minutes under the following dissolution conditions: DI water, 500 mL, USP Apparatus 2 (Paddle), 50 rpm, 37° C.

9. The orally administrable pharmaceutical composition of claim 1, wherein the drug is oxycodone hydrochloride.

10. An orally administrable pharmaceutical composition in unit dosage form comprising:
a barrier layer comprising a barrier polymer comprising a copolymer of ethyl acrylate and methyl methacrylate;
a diffusion layer covering the barrier layer and comprising a drug selected from the group consisting of oxycodone or pharmaceutically acceptable salts thereof, and a diffusion polymer comprising a copolymer of ethyl acrylate and methyl methacrylate; and
an outer coating covering the diffusion layer and comprising a pH-independent agent comprising ethylcellulose, and a pH-dependent agent comprising a cationic polymer comprising dimethylaminoethyl methacrylate, wherein the unit dosage form is a tablet, wherein the pharmaceutical composition does not comprise an opioid antagonist, mucous membrane irritant, or emetic, wherein the weight ratio of pH-dependent agent to pH-independent agent is about 10:1 to 10:6, wherein the outer coating does not comprise a drug and wherein the composition is configured such that when the pharmaceutical composition is administered intranasally in crushed form to a subject, a ratio of the area under the curve (AUC) of the drug to the AUC of a major metabolite of the drug (drug major metabolite) achieved after a period of time is about 10 or less; and wherein said cationic polymer with a dimethylaminoethyl group is poly (butyl methacrylate-co-(2-dimethylaminethyl) methacrylate-co-methyl methacrylate.

11. The orally administrable pharmaceutical composition of claim 10, wherein the composition is such that when the pharmaceutical composition is administered intranasally in crushed form to a subject, the ratio of the $AUC_{0-t}$ of the drug to the $AUC_{0-t}$ of a major metabolite of the drug (drug major metabolite) achieved after a period of time is about 0.1 to about 4.

12. The orally administrable pharmaceutical composition of claim 10, wherein the drug is oxycodone hydrochloride.

13. The orally administrable composition of claim 10, wherein the composition is such that about 60% or more of the total amount of drug in the pharmaceutical composition is released after 60 minutes under the following dissolution conditions: 0.1 N HCl, 500 mL, USP Apparatus 2 (paddle), 50 rpm, 37° C.; and wherein about 25% or less of the total amount of drug in the pharmaceutical composition is released after 60 minutes under the following dissolution conditions: DI water, 500 mL, USP Apparatus 2 Paddle), 50 rpm, 37° C.

14. The orally administrable composition of claim 10, wherein the composition is such that no more than 50% of the total amount of drug in the pharmaceutical composition is released within 1 hour and about 50% or more of the total mount of drug in the pharmaceutical composition is released after 8 hours under the following dissolution conditions: 0.1 N HCl, 500 mL, USP Apparatus 2 (paddle), 50 rpm, 37° C.; and wherein about 25% or less of the total amount of drug is released after 60 minutes under the following dissolution conditions: DI water, 500 mL, USP Apparatus 2 (Paddle), 50 rpm, 37° C.

15. The orally administrable composition of claim 1, wherein the weight ratio of pH-dependent agent to pH-independent agent is about 10:2 to 10:4.

16. The orally administrable composition of claim 10, wherein the weight ratio of pH-dependent agent to pH-independent agent is about 10:2 to 10:4.

17. The orally administrable composition of claim 1, wherein the pH-independent agent comprises ethylcellulose polymer having a viscosity of about 41-49.

18. The orally administrable composition of claim 10, wherein the pH-independent agent comprises an ethylcellulose polymer having a viscosity of 41-49.

19. The orally administrable composition of claim 1, which further comprises a filler, glidant, surfactant, lubricant and plasticizer.

20. The orally administrable composition of claim 10, which further comprises a filler, glidant, surfactant, lubricant and plasticizer.

* * * * *